(12) United States Patent
Ory et al.

(10) Patent No.: US 9,012,216 B2
(45) Date of Patent: *Apr. 21, 2015

(54) METHODS OF DETERMINING EFFICACY OF CYCLODEXTRIN THERAPY

(71) Applicants: Washington University, Saint Louis, MO (US); The United States of America, National Institutes of Health, as represented by the Sec. Dept HHS, Bethesda, MD (US)

(72) Inventors: Daniel S Ory, Saint Louis, MO (US); Forbes Porter, Gaithersburg, MD (US)

(73) Assignees: Washington University, Saint Louis, MO (US); US National Institutes of Health, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/786,757

(22) Filed: Mar. 6, 2013

(65) Prior Publication Data

US 2013/0177990 A1 Jul. 11, 2013

Related U.S. Application Data

(63) Continuation of application No. 12/385,529, filed on Apr. 10, 2009, now Pat. No. 8,497,122.

(60) Provisional application No. 61/071,074, filed on Apr. 11, 2008.

(51) Int. Cl.
*C12N 5/071* (2010.01)
*G01N 33/92* (2006.01)
*G01N 33/68* (2006.01)

(52) U.S. Cl.
CPC ............ *G01N 33/92* (2013.01); *G01N 33/6893* (2013.01); *G01N 33/6896* (2013.01); *G01N 2800/044* (2013.01); *G01N 2800/2857* (2013.01); *G01N 2800/52* (2013.01); *G01N 2800/56* (2013.01)

(58) Field of Classification Search
CPC .................................................... G01N 33/6893
USPC ............................................................. 435/11
See application file for complete search history.

(56) References Cited

PUBLICATIONS

Loftsson et al. "Cyclodextrins in drug delivery", Expert Opin. Drug Deliv., 2005, 2:335-351.*
Umetani et al. "27-hydroxycholesterol is an endogenous SERM that inhibits the cardiovascular effects of estrogen", Nature Medicine, 2007, 13(10):1185-1192.*

* cited by examiner

*Primary Examiner* — Bin Shen
(74) *Attorney, Agent, or Firm* — Saul L. Zackson; Zackson Law LLC

(57) ABSTRACT

Disclosed are methods for determining efficacy of a cyclodextrin therapy in a subject afflicted with a disorder involving oxysterol accumulation. These methods comprise: obtaining a first body fluid sample from the subject prior to cyclodextrin administration; administering cyclodextrin; obtaining at least one second body fluid sample after the cyclodextrin administration; subjecting the body fluid samples to chromatography-mass spectroscopy analysis to determine concentration of 24-hydroxycholesterol and/or cholestane-3β,5α,6β-triol; and determining magnitude of difference between the 24-hydroxycholesterol and/or cholestane-3β,5α,6β-triol concentration of the body fluid samples, whereby an increase or stabilization of 24-hydroxycholesterol concentration, or a reduction of cholestane-3β,5α,6β-triol concentration in the at least one second sample compared to the first sample, indicates efficacy of the cyclodextrin therapy.

20 Claims, 17 Drawing Sheets

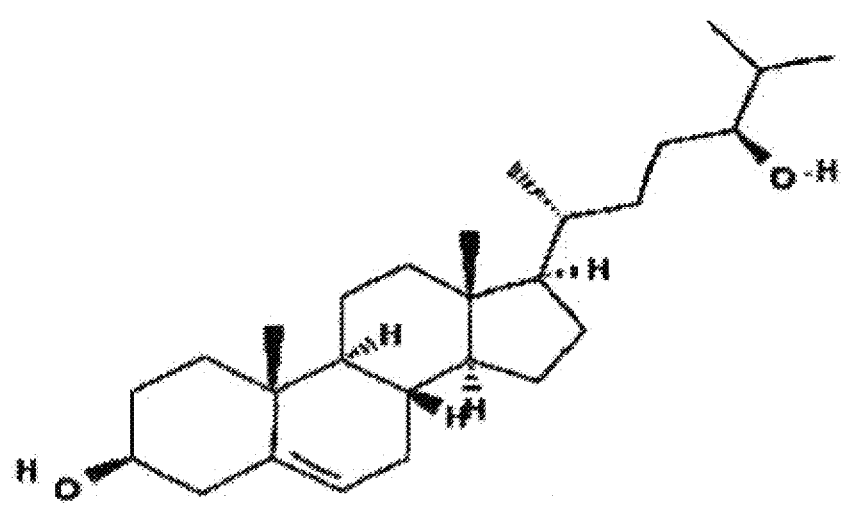
Prior Art FIG. 1A

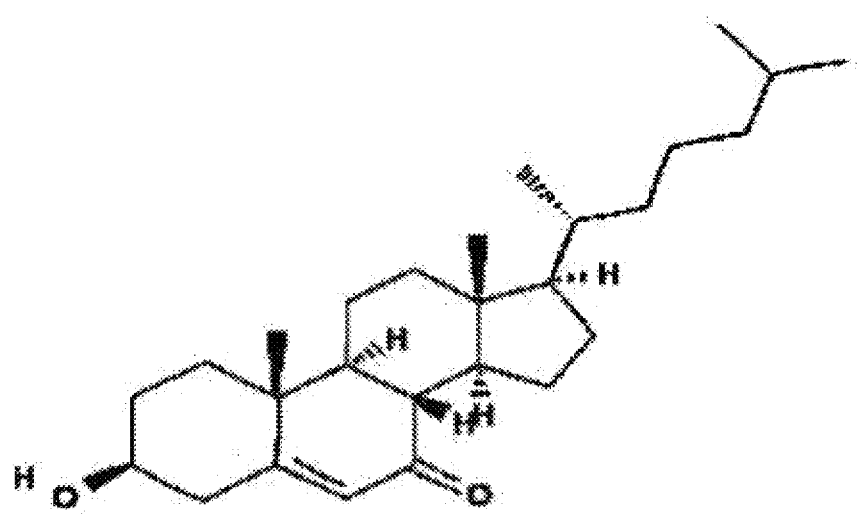
Prior Art FIG. 1B

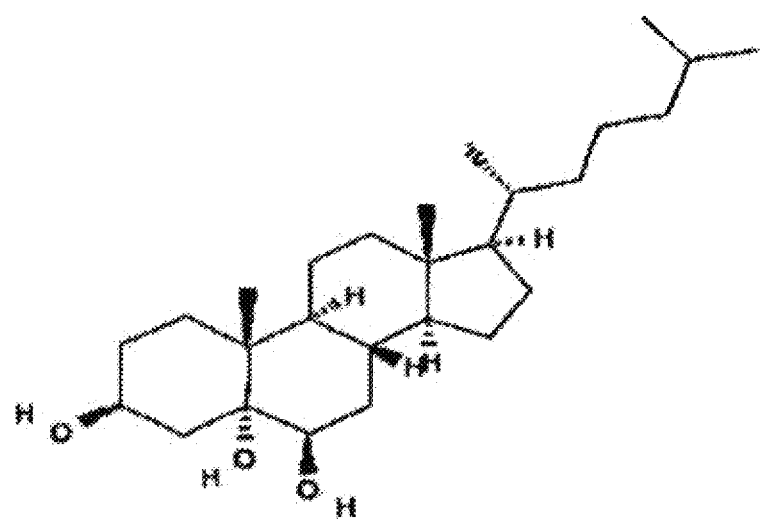
Prior Art FIG. 1C

CONTROL
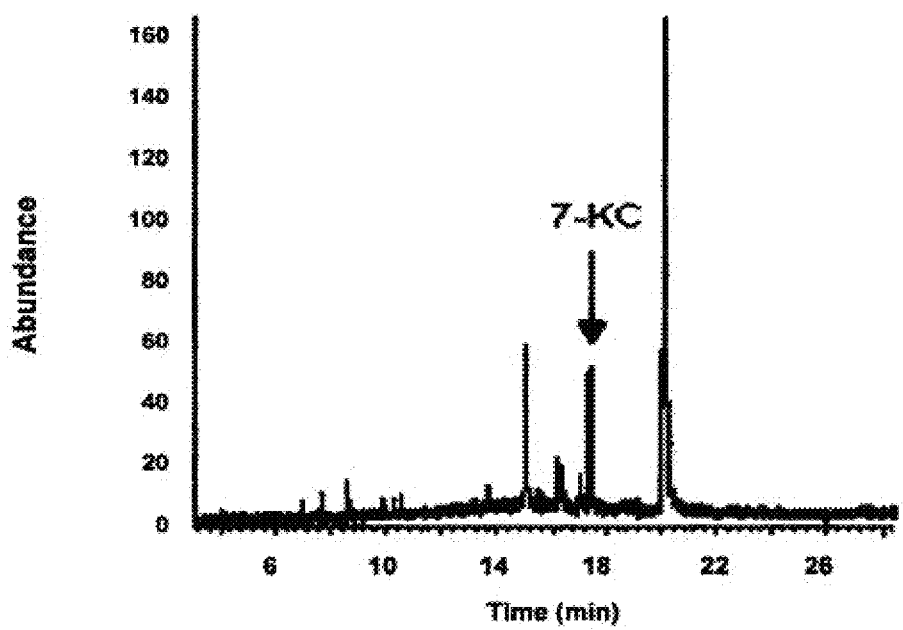
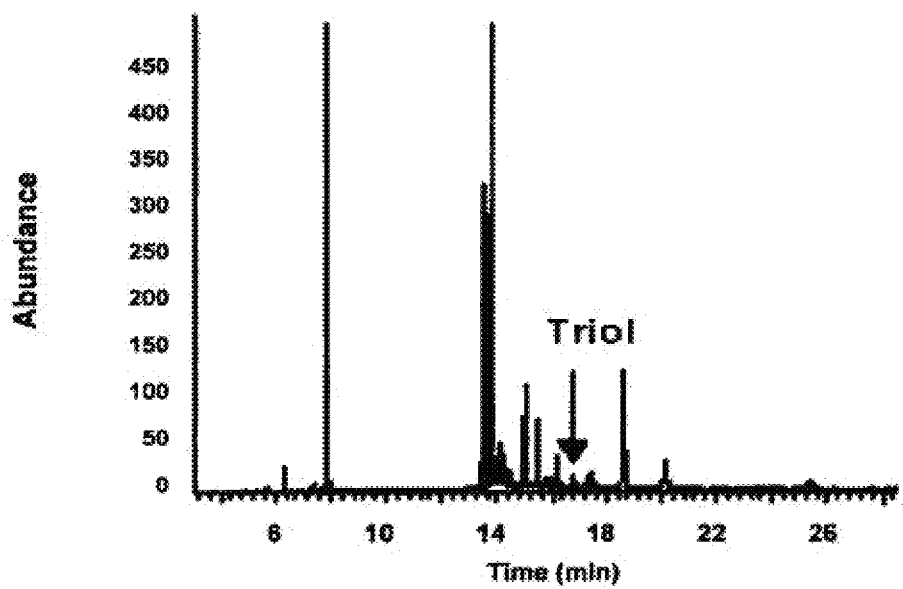
FIG. 2C

METHODS OF DETERMINING EFFICACY OF CYCLODEXTRIN THERAPY

CROSS-REFERENCE TO RELATED APPLICATIONS

This application is a continuation of U.S. Non-Provisional Application No. 12/385,529, now U.S. Pat. No. 8,497,122, filed on Apr. 10, 2009, which claims the benefit of U.S. Provisional Application No. 61/071,074, filed on Apr. 11, 2008. The disclosures of the applications above are incorporated herein by reference in their entirety.

GOVERNMENT RIGHTS

This disclosure was made with government support under Grant No. P50 HL083762 from the National Institutes of Health. The Government has certain rights in the invention.

FIELD

The present disclosure relates to biomarkers for disorders involving accumulation of one or more oxysterols such as cytotoxic oxysterol accumulation, Niemann-Pick C (NPC) disease, lysosomal storage diseases, cholesterol trafficking diseases, and neurodegenerative diseases.

INTRODUCTION

The statements in this section merely provide background information related to the present disclosure and may not constitute prior art.

Niemann-Pick type C (NPC) disease is an autosomal recessive lysosomal storage and neurodegenerative disorder. It can involve accumulation of cholesterol and other lipids in the viscera and the central nervous system, and patterned Purkinje cell death in the cerebellum. NPC disease is described, for example, on the On-Line Mendelian Inheritance in Man ("OMIM") website, at OMIM number 257220. NPC presents a highly variable clinical phenotype. In childhood-onset NPC, the patients typically appear normal for 1 or 2 years with neurological symptoms, such as ataxia, grand mal seizures, loss of previously learned speech, spasticity, and seizures, appealing at 2 to 4 years. There are also prenatal and adult-onset forms of the disease.

In NPC disease, two genetic complementation groups, NPC 1 and NPC2, have been identified. Mutations in the NPC 1 gene cause ~95% of the cases, the rest being caused by NPC2 mutations. NPC2 is a soluble, glycosylated protein that is present in the lumen of the late endosome. "Loss-of-function of the NPC 1 gene in mice yields marked impairment in both esterification of low-density lipoprotein (LDL) cholesterol and mobilization of newly hydrolyzed LDL cholesterol to the plasma membrane, resulting in lysosomal sequestration of LDL cholesterol, delayed down-regulation of the LDL receptor and de novo cholesterol biosynthesis, and impaired ATP-binding cassette transporter (ABCA1)-mediated cholesterol efflux. Associated with these lipid trafficking defects, NPC 1 mutants exhibit cellular oxidative stress, leading to increased production of non-enzymatic cholesterol auto-oxidation products.

Information regarding the biochemical and histopathological defects associated with NPC has come through the use of two murine models which share many of the clinical abnormalities observed in humans with NPC: elevated levels of sphingomyelin and unesterified cholesterol in liver and spleen, presence of foamy macrophages, neuronal vacuoles, focal axonal swelling, and decreased Purkinje cell number. The two murine NPC models, C57B1Ks/J spm and BALB/c npc$^{nih}$, arose as spontaneous mutations, were determined allelic by cross breeding, and have been independently localized to mouse chromosome 18 in a region synthetic to the human NPC1 locus. Confirmation that the two mouse loci belong to the same complementation group as the human NPC 1 locus was determined using heterokaryon fusions of human NPC 1 fibroblasts to mouse mutant cell lines and by DNA-mediated complementation using a yeast artificial chromosome (YAC) from the human NPC 1 region. Combined, these studies indicate that the same gene is altered in the two mouse NPC models (spm and npcnih) and that the orthologous gene in the mouse models is defective at the human NPC1 locus.

Despite recent progress in characterizing the biochemical and genetic defects in NPC disease, the mean time to diagnosis from initial presentation is approximately five years. The delay in diagnosis is largely due to the lack of both newborn screening and disease biomarkers, as well as the lack of widely available diagnostic tests. In addition, the absence of biomarkers that correlate with disease severity has hampered evaluation of the efficacy of therapeutic approaches to NPC disease.

DRAWINGS

The drawings described herein are for illustration purposes only and are not intended to limit the scope of the present disclosure in any way.

FIG. 1A shows the chemical structure of 24(S) hydroxycholesterol (herein referred to as "24HC")

FIG. 1B shows the chemical structure of 7-ketocholesterol (herein referred to as '7-keto").

FIG. 1C shows the chemical structure of cholestane-3β,5α, 6β-triol (herein referred to as "triol").

FIGS. 2A-2D show gas chromatogram/mass spectra (GC/MS) of oxysterols in plasma samples obtained from confirmed NPC patients and control non-NPC afflicted subjects. The arrows indicate oxysterol biomarker identification. The Y-axis is the measure of relative abundance of sampled oxysterols measured against a known internal standard from which a calculation of the concentration of the oxysterol in the biological sample can be made. The X-axis is the retention time of each of the ion species eluting from the GC column in minutes. The table below the control and NPC samples summarizes the relative abundance of each oxysterol measured using the identification and testing methods of the present disclosure in the NPC disease group and the control group.

Figure 2A:
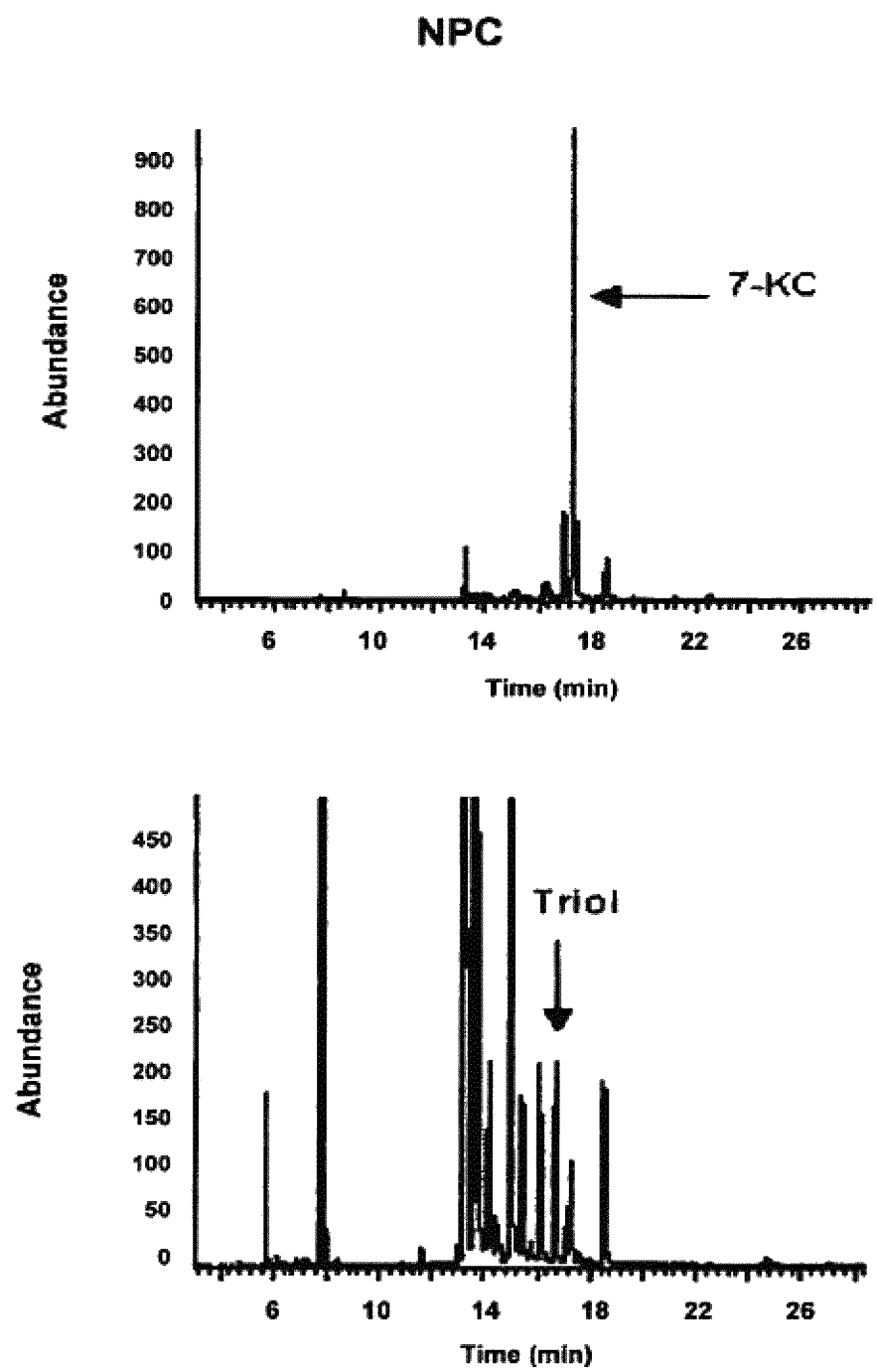
Figure 2B:
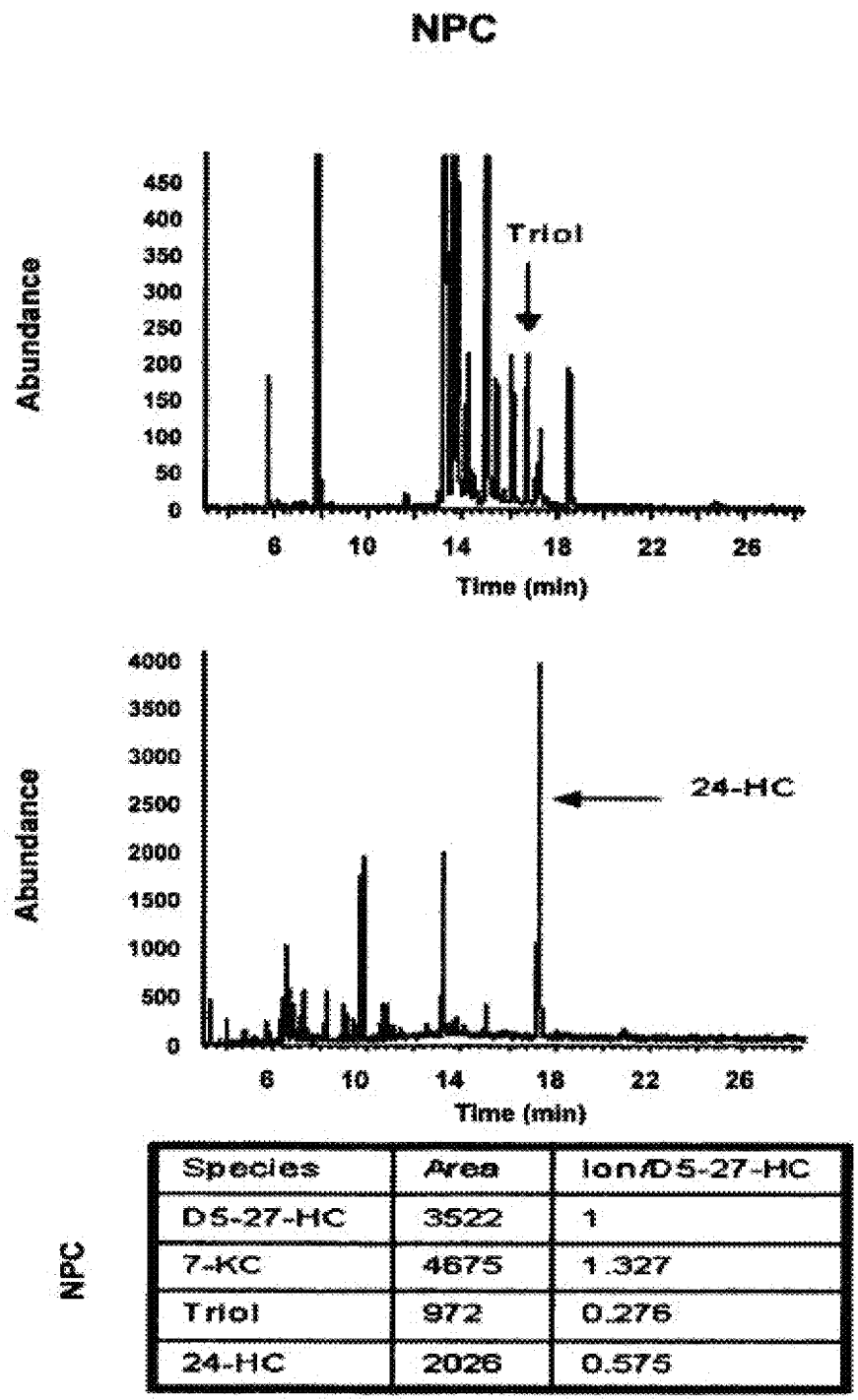
Figure 2D:
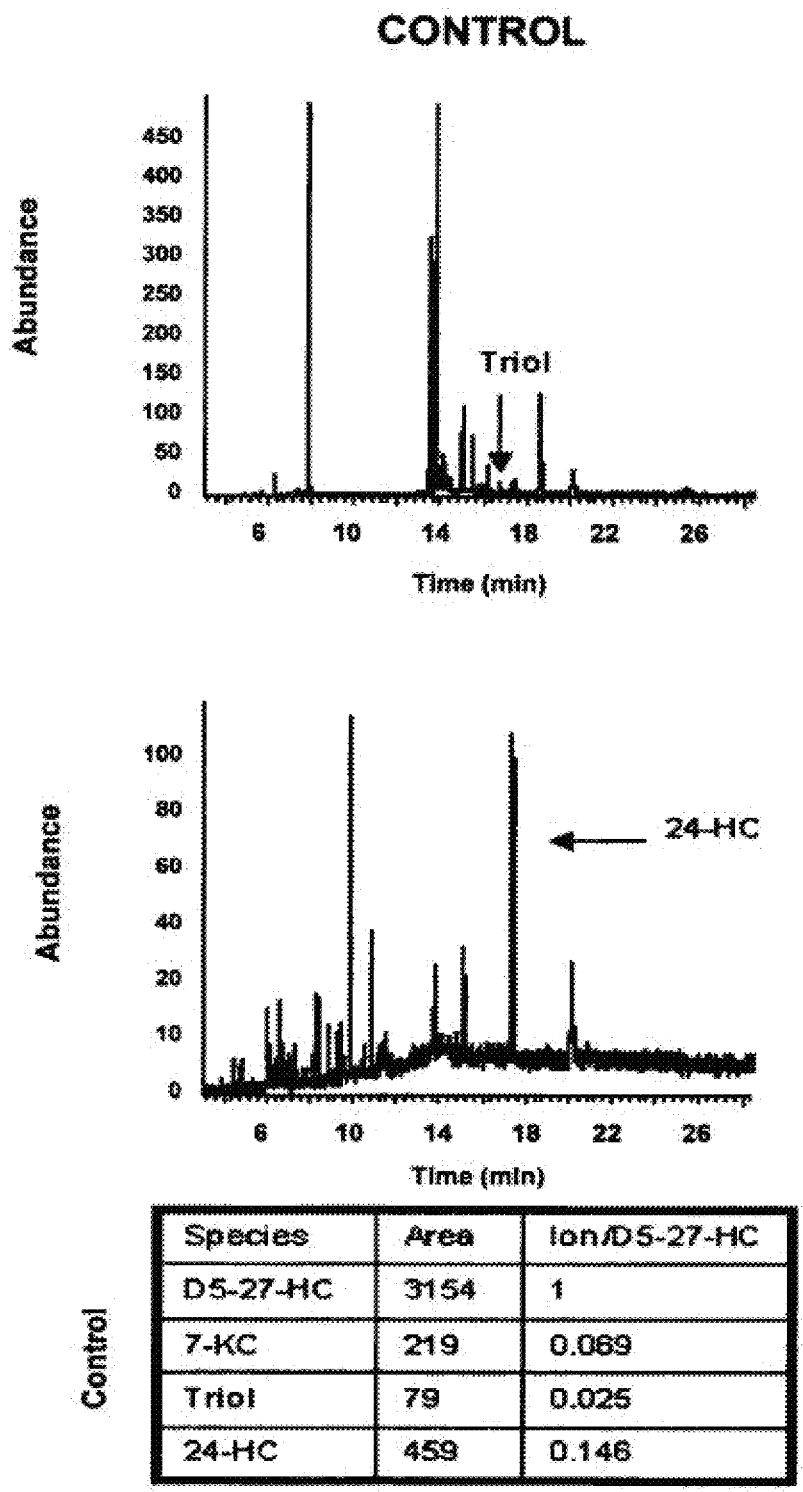
Figure 3:
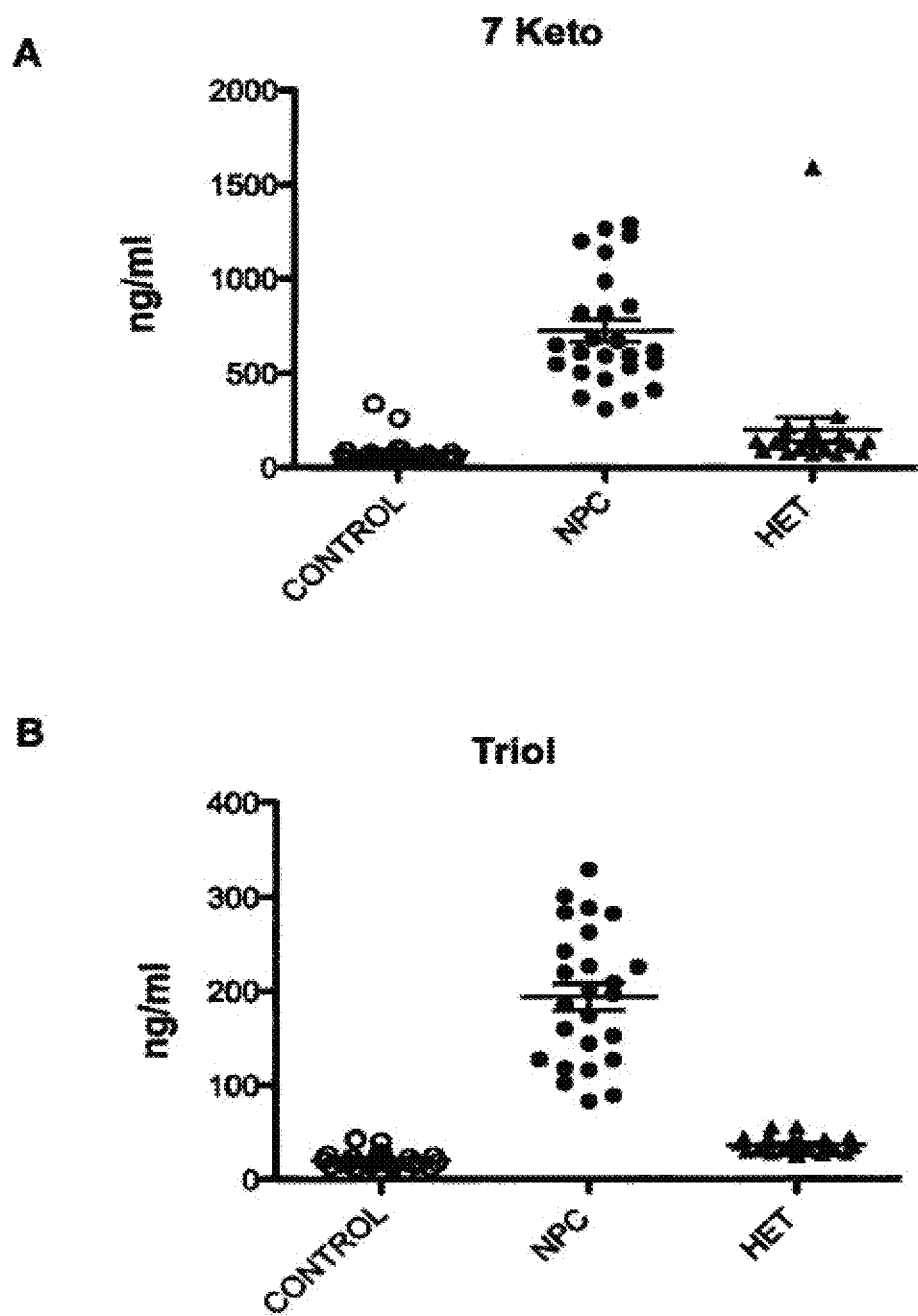

FIG. 3A shows a graph depicting plasma levels of the oxysterol 7-keto obtained from control non-afflicted subjects ("CONTROL"), confirmed NPC subjects ("NPC"), and heterozygote but not NPC-afflicted subjects having a NPC 1 +/− genotype ("HET"). The concentration of the oxysterol 7-keto is expressed as nanograms per milliliter (ng/mL) of plasma.

FIG. 3B shows a graph depicting plasma levels of the oxysterol triol obtained from control non-afflicted subjects ("CONTROL"), confirmed NPC subjects ("NPC"), and obligate or confirmed heterozygote non-NPC afflicted subjects having a NPC 1 +/− genotype ("HET"). The concentration of the oxysterol triol is expressed as nanograms per milliliter (ng/mL) of plasma.

Figure 4:
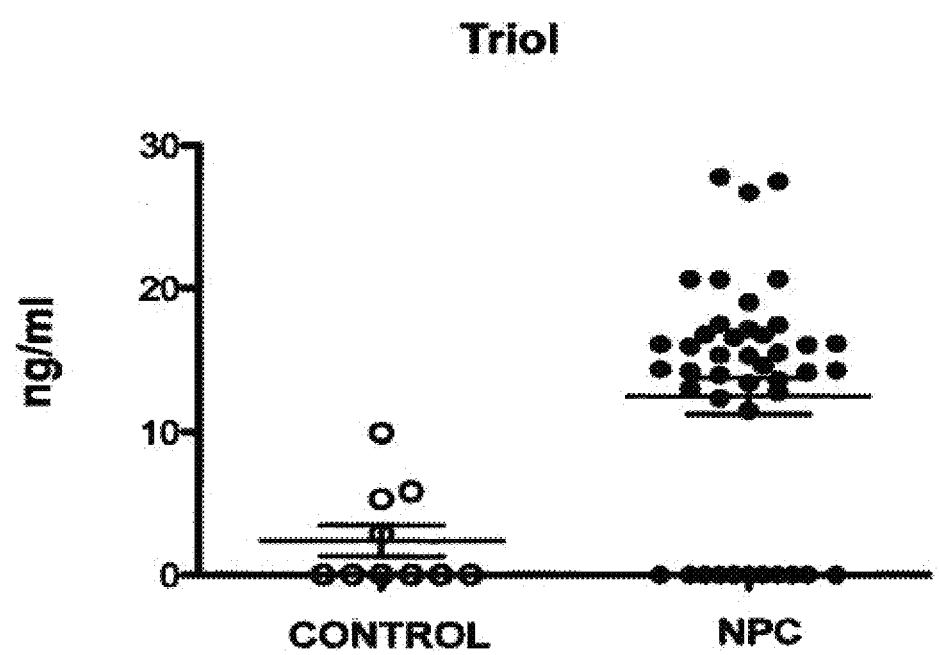

FIG. 4 shows a graph depicting levels of the oxysterol triol from cerebrospinal fluid (CSF) samples obtained from control non-afflicted subjects ("CONTROL") and confirmed NPC subjects ("NPC"). The concentration of the oxysterol triol is expressed as nanograms per milliliter (ng/mL) of plasma.

Figure 5:
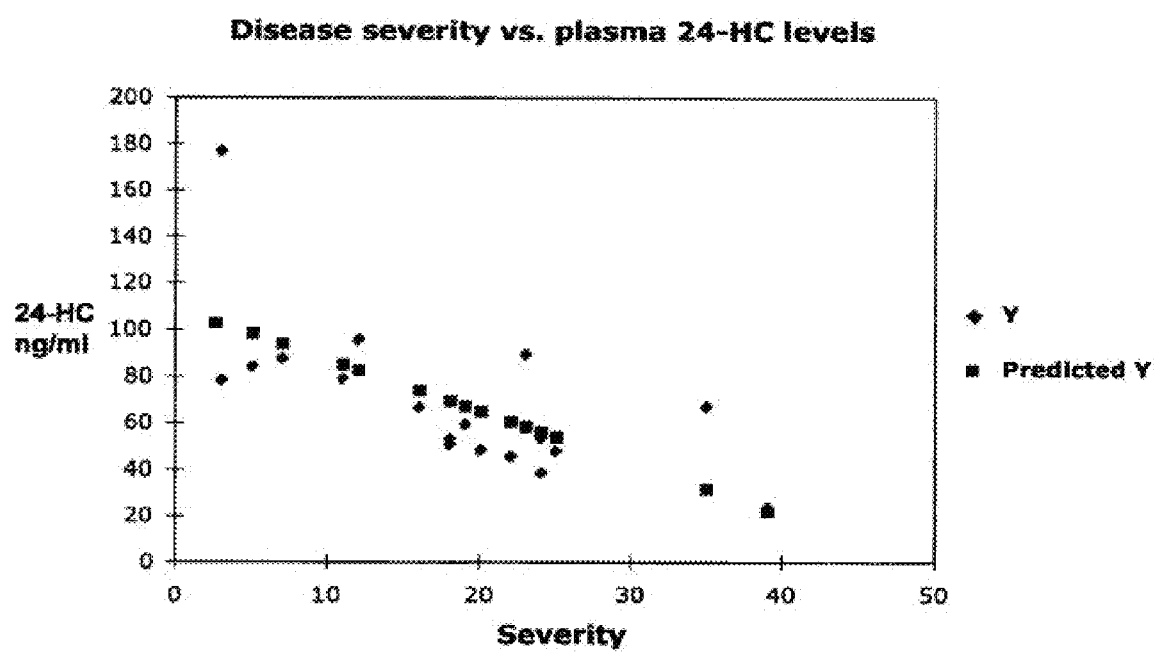

FIG. 5 shows a Pearson Correlation coefficient for the correlation between disease severity and plasma levels of 24-HC.

Figure 6:
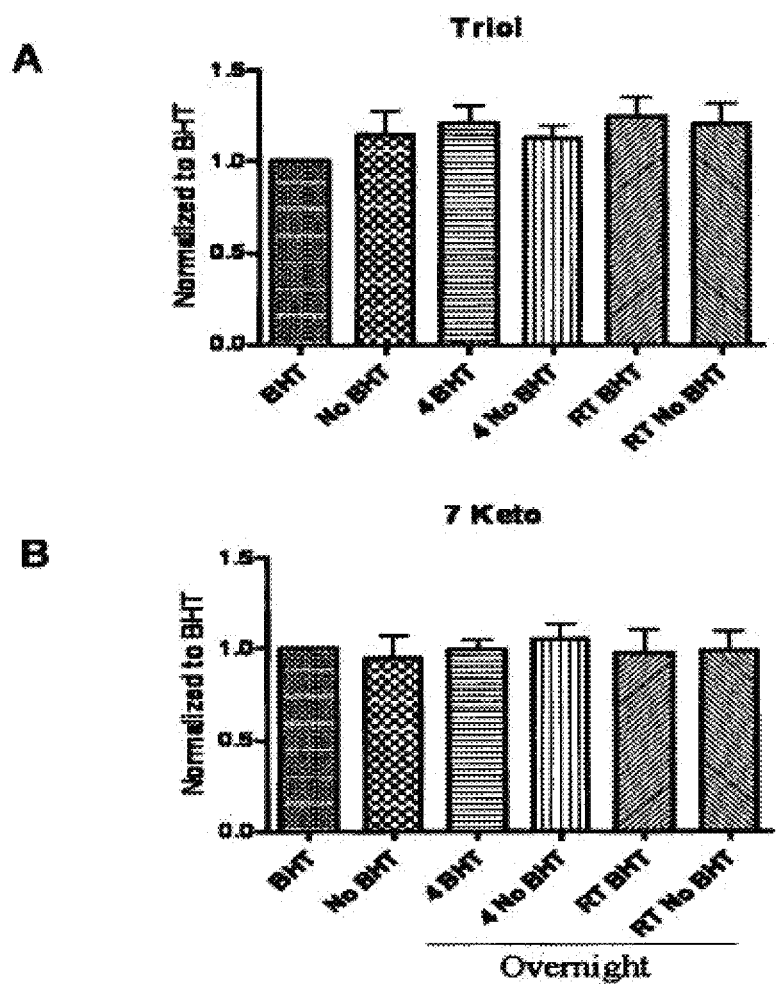

FIG. 6A shows a bar graph depicting the concentration of triol normalized to the concentration of triol from NPC plasma samples treated with butylated hydroxytoluene (BHT). Treatments include: NPC plasma samples treated with BHT ("BHT"), no BHT ("No BHT"), at 4° C. with BHT ("4 BHT"), at 4° C. without BHT ("4 No BHT"), at room temperature (20-21° C.) with BHT ("RT BHT"), and at room temperature (20-21° C.) without BHT ("RT No BHT").

FIG. 6B shows a bar graph depicting the relative concentration of 7-keto normalized to the concentration of 7-keto from NPC plasma samples treated with butylated hydroxytoluene (BHT). Treatments include: NPC plasma samples treated overnight with BHT ("BHT"), no BHT ("No BHT"), at 4° C. with BHT ("4 BHT"), at 4° C. without BHT ("4 No BHT"), at room temperature (20-21° C.) with BHT ("RT BHT"), and at room temperature (20-21° C.) without BHT ("RT No BHT").

Figure 7:
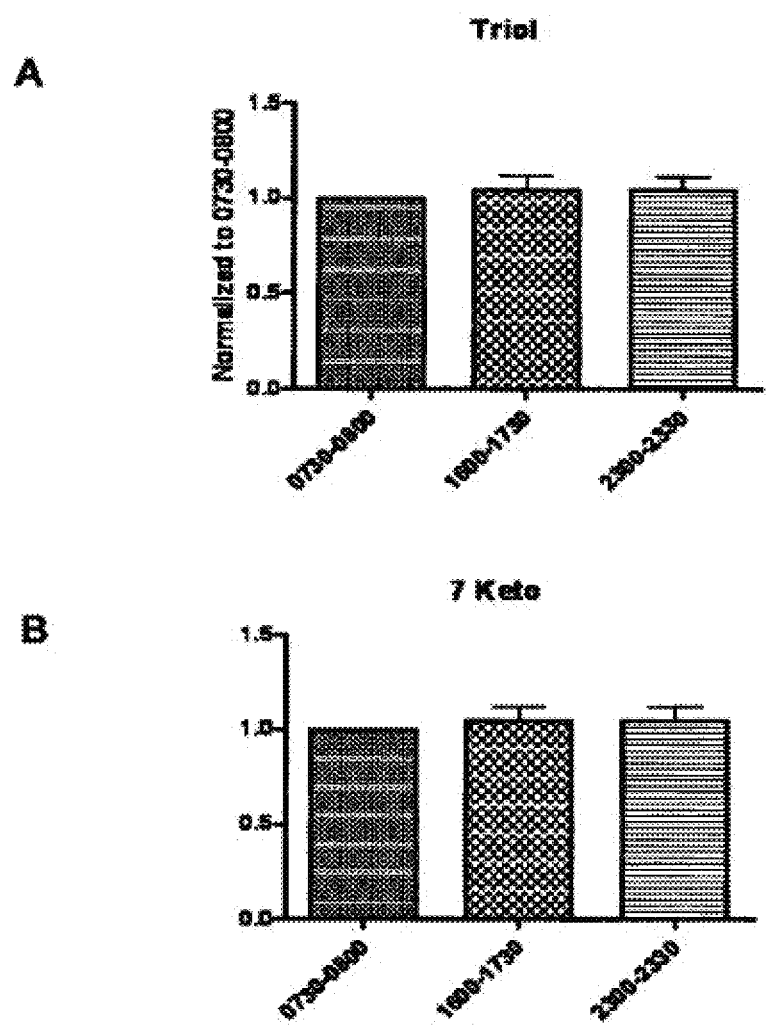

FIG. 7A shows a bar graph depicting the relative amount of triol from NPC subjects normalized to amounts of triol in plasma samples obtained between the hours of 7:30 am-8:00 am ("0730-0800"). Other timed intervals include between 4:00 pm and 5:30 ("1600-1730") and between 11:00 pm and 11:30 pm ("2300-2330"). Results are indicative of averaged values over 5 different measurements for each time point.

FIG. 7B shows a bar graph depicting the relative amount of triol from NPC subjects normalized to amounts of triol in plasma samples obtained between the hours of 7:30 am-8:00 am ("0730-0800"). Other timed intervals include between 4:00 pm and 5:30 ("1600-1730") and between 11:00 pm and 11:30 pm ("2300-2330"). Results are indicative of averaged values over 5 different measurements for each time point.

Figure 8:
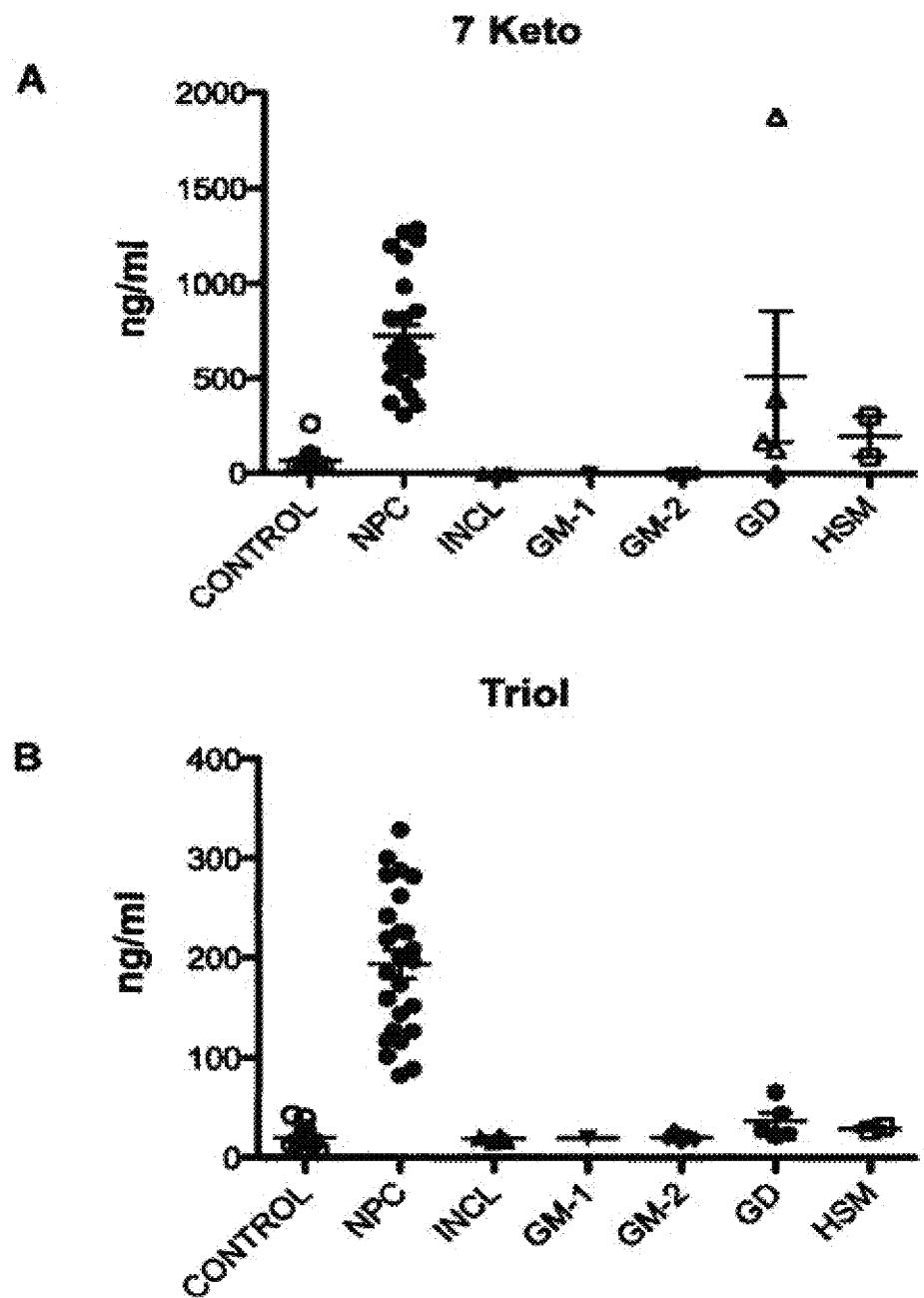
Figure 9A:
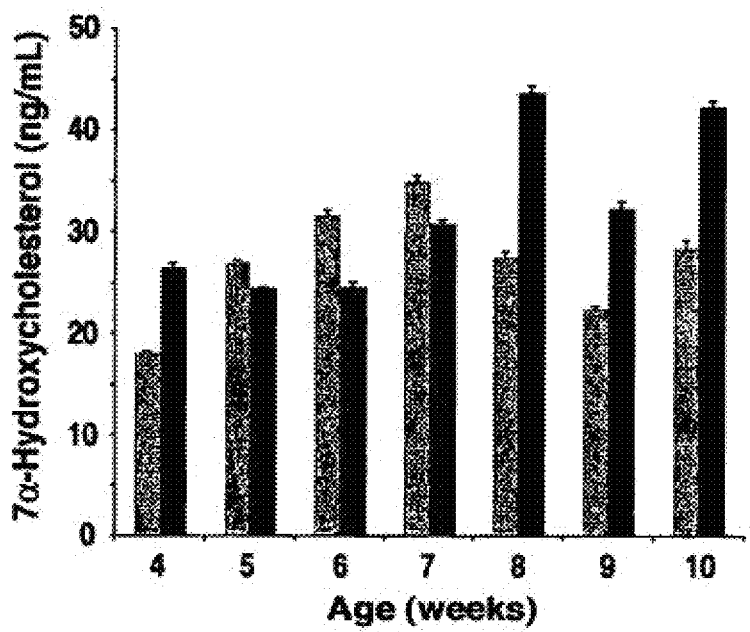
Figure 9B:
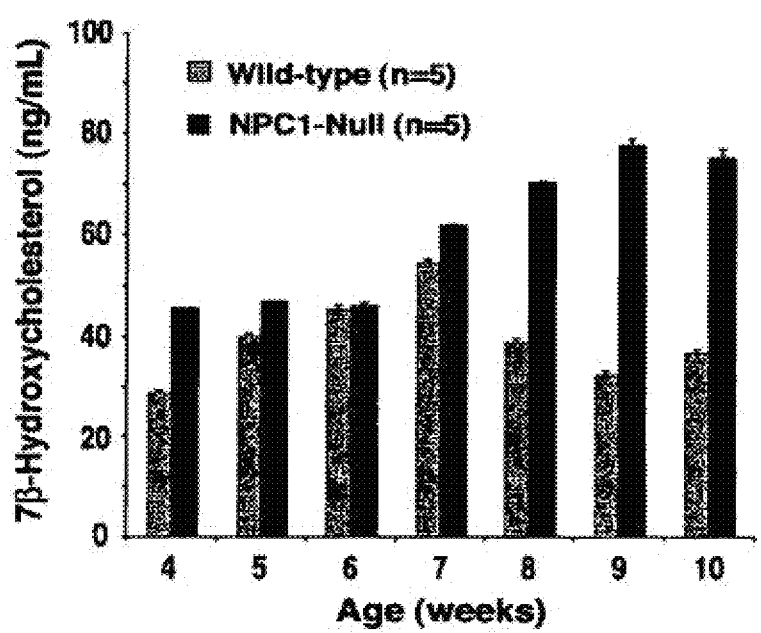
Figure 9C:
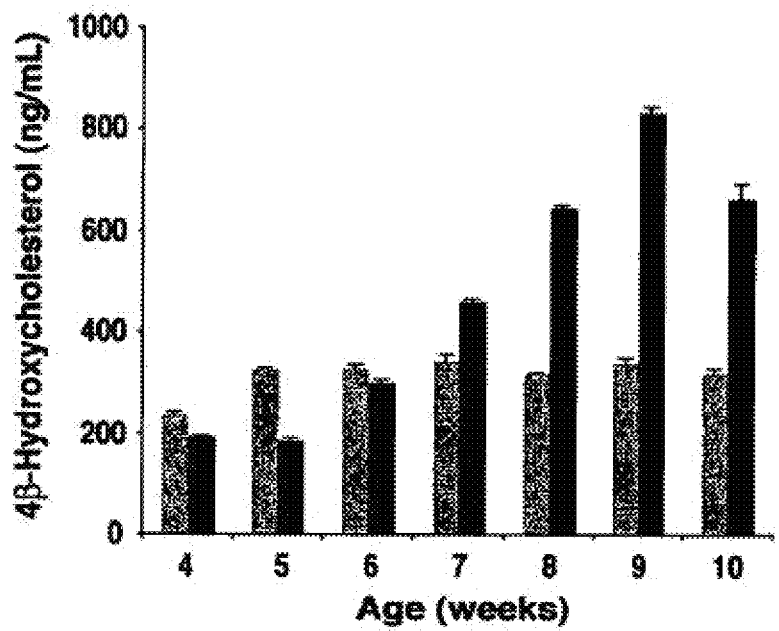
Figure 9D:
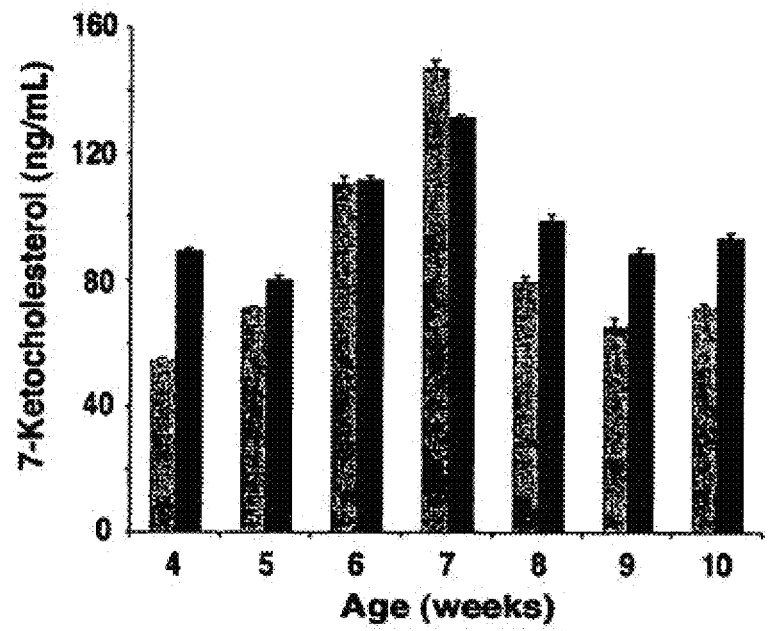
Figure 9E:
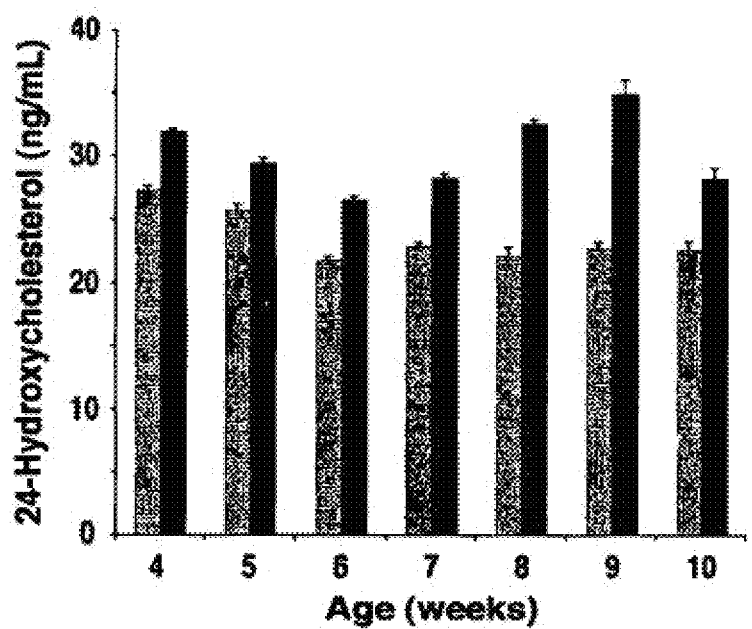
Figure 9F:
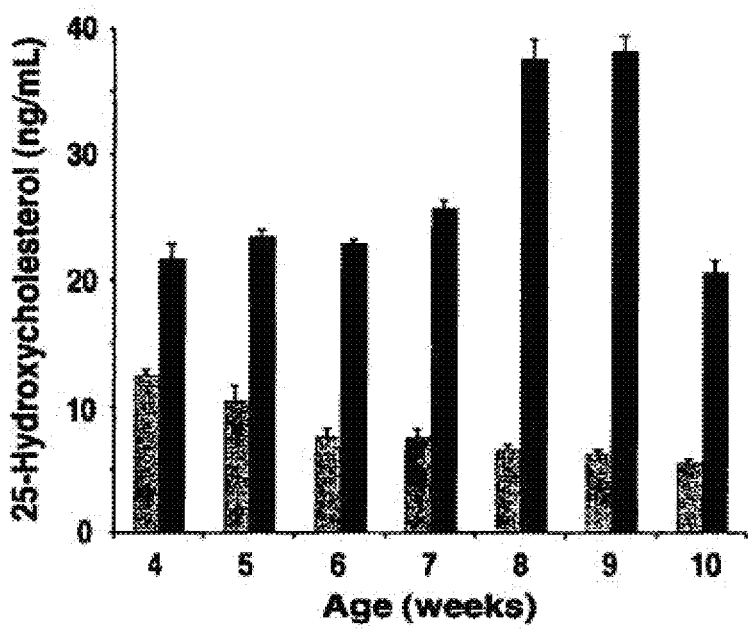
Figure 9G:
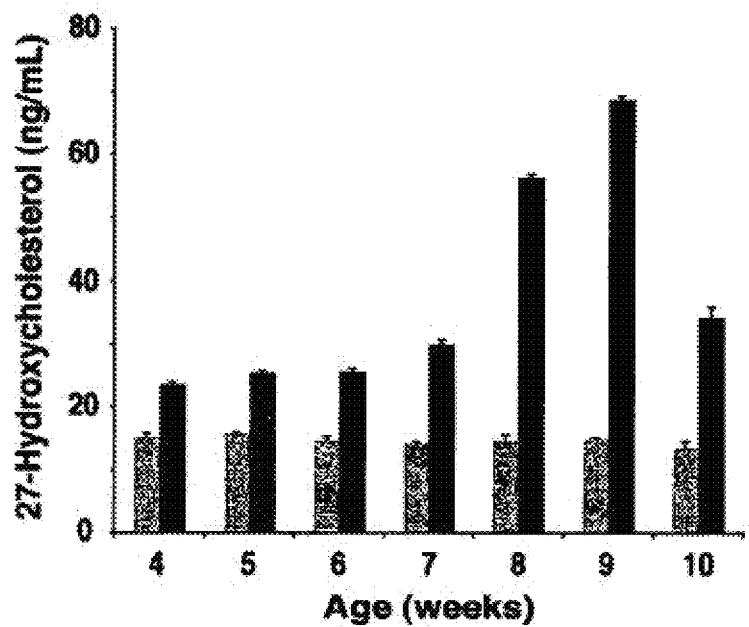
Figure 9H:
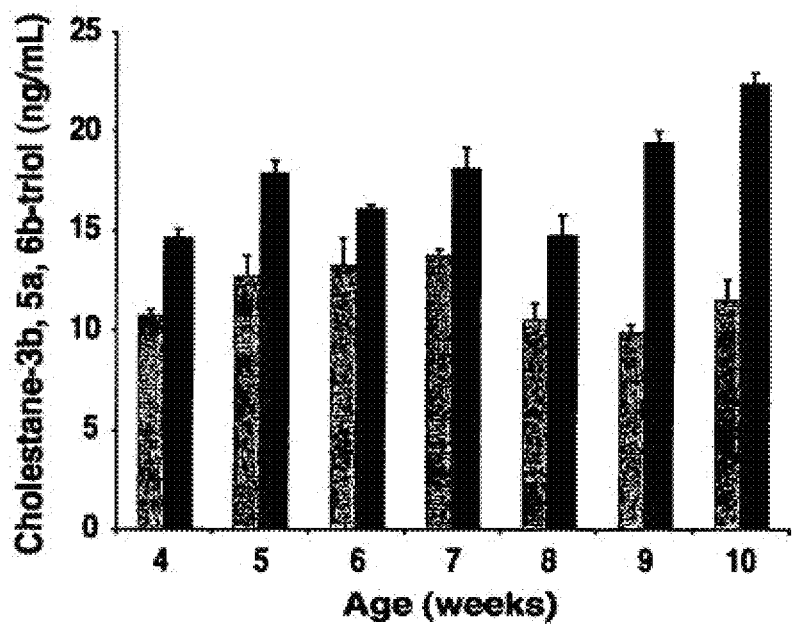

FIG. 8A shows a graph depicting plasma levels of the oxysterol 7-keto obtained from control non-afflicted subjects ("CONTROL"), confirmed NPC subjects ("NPC") and from subjects having other lysosomal storage diseases, including those with known CNS involvement: infantile neuronal ceroid lipofuscinosis ("INCL"), GM1 gangliosidosis ("GM-1"), GM-2 gangliosidosis ("GM-2") (Tay-Sachs Disease), Gaucher's disease ("GO") and hepatosplenomegaly ("HSM"). The concentration of the oxysterol 7-keto and triol are expressed as nanograms per milliliter (ng/mL) of plasma.

FIG. 8B shows a graph depicting plasma levels of the oxysterol triol obtained from control non-afflicted subjects ("CONTROL"), confirmed NPC subjects ("NPC") and from subjects having other lysosomal storage diseases, including those with known CNS involvement: infantile neuronal ceroid lipofuscinosis rINCL"), GM1 gangliosidosis ("GM-1"), GM-2 gangliosidosis ("GM-2") (Tay-Sachs Disease), Gaucher's disease ("GD") and hepatosplenomegaly ("HSM"). The concentration of the oxysterol triol is expressed as nanograms per milliliter (ng/mL) of plasma.

FIGS. 9A-9H show bar graphs of oxysterols 24-hydroxycholesterol ("24-HC"), 25-hydroxycholesterol ("25-HC"), 27-hydroxycholesterol ("27-HC"), cholestane-3β,5α,6β-triol ("triol"), 4β-hydroxycholesterol ("4β-HC"), 7α-hydroxycholesterol ("7α-HC"), 7β-hydroxycholesterol ("7β-HC"), and 7-ketocholesterol ("7-keto") isolated from wild-type and NPC1−/− null mice (NPC afflicted mice) as a function of age (weeks). Methods for isolating, identifying and quantifying the various oxysterols were in accordance with the present disclosure.

SUMMARY

The present disclosure relates to the finding that one or more of a set of oxysterols may be used as a biomarker for screening, diagnosing, or monitoring disorders involving accumulation of one or more oxysterols such as cytotoxic oxysterol accumulation, Niemann-Pick C (NPC) disease, lysosomal storage disease, and neurodegenerative disease. Oxysterols are commonly referred to as oxidized derivatives of cholesterol, typically generated non-enzymatically, enzymatically as a normal part of cholesterol metabolism, or absorbed through dietary intake. Oxysterols typically have a hydroxyl-, epoxy or a keto-group on the cholesterol molecule. In some embodiments of the present disclosure, the oxysterol can be anyone or more of 24(S)hydroxycholesterol ("24-HC"), 25-hydroxycholesterol (25-HC), 7-ketocholesterol ("7-keto") and cholestane-3β,5α,6β-triol ("triol").

An oxysterol ma be present in a subject at a level that is elevated compared to the level of the oxysterol in a population not afflicted with a disorder involving accumulation of one or more oxysterols such as cytotoxic oxysterol accumulation, NPC disease, lysosomal storage diseases, cholesterol trafficking diseases, and neurodegenerative diseases. Certain oxysterols can be present at levels below those found in control populations, and/or at levels that vary over time. Levels of oxysterols can be used for screening, diagnosing, and/or monitoring disorders involving accumulation of one or more oxysterols such as cytotoxic oxysterol accumulation, NPC disease, lysosomal storage diseases, cholesterol trafficking diseases, and neurodegenerative diseases.

The present disclosure provides methods for identifying a subject having, or at risk for developing, NPC disease by detecting an increased concentration of one or more oxysterols in a biological sample collected from the subject. The present disclosure provides methods for screening or diagnosing subjects (including infants and neonatal subjects) for NPC disease. Also disclosed are methods for monitoring the progression, remission, and clinical status of NPC disease and for evaluating the efficacy of therapeutic treatment of NPC disease.

DESCRIPTION OF VARIOUS EMBODIMENTS

The following description is merely exemplary in nature and is not intended to limit the present disclosure, application, claims, compounds, or uses.

A. Oxysterols: Biomarkers for NPC Disease and Other Disorders.

An oxysterol may be present in a subject at a level that is elevated compared to the level of the oxysterol in subjects' not afflicted with a disorder involving accumulation of one or more oxysterols such as cytotoxic oxysterol accumulation, NPC disease, lysosomal storage disease, cholesterol trafficking diseases, and neurodegenerative diseases. An oxysterol level can correlate with, and serve as a biomarker for, the presence, progression, or risk of developing one or more such disease states. Those skilled in the art will appreciate that some oxysterol levels may be higher in patients with early onset of NPC disease as compared with later onset forms of the disease.

In some embodiments, an elevated oxysterol useful as an indicator of disease or risk of developing disease can be anyone or more of 24(S)-hydroxycholesterol ("24-HC"), 25-hydroxycholesterol (25-HC), 7-ketocholesterol ("7-keto"), and cholestane-3β,5α,6β-triol ("triol"). Biomarkers can also include other oxysterol species that are abnormally elevated in disorder involving accumulation of one or more oxysterols such as cytotoxic oxysterol accumulation, NPC disease, lysosomal storage disease, cholesterol trafficking diseases, and neurodegenerative diseases. Oxysterols that correlate with NPC disease are shown in FIGS. 1A, 1B and 1C.

Without being bound by theory, and without limiting the scope of the disclosure or claims, it is presently hypothesized that the presence of elevated levels of oxysterols in peripheral and neural cells occurs as a result of autooxidation or normal enzymatic degradation of cholesterol, as a product of oxidative stress, and through dietary intake. With respect to 24-HC, it is presently hypothesized that this particular metabolite, also known as cerebrosterol, is produced as a result of 24(S)-hydroxylation of cholesterol in the cerebral cortex, hippocampus, dentate gyrus and thalamus.

The production of 24-HC is presently hypothesized to occur as a natural mechanism for cholesterol release from the brain, and the exchange of 24-HC from the brain to the circulation is thought to be a continuous age-dependent flux of about 4 mg/day. Other hydroxylases in the neuron may also be responsible for the conversion of cholesterol to 7-keto. Evidence presently suggests that the increased levels of the oxysterols 24-HC, 7-keto and triol in the plasma and cerebrospinal fluid might correlate with reactive species generation and 24-HC, 7-keto and triol indicative of lipid trafficking defects in neurons and other peripheral tissues, for example, the liver, spleen, kidney and in leukocytes. It is therefore presently hypothesized that elevated oxysterol concentrations in body fluids (e.g., blood, plasma, serum, cerebrospinal fluid, cell membrane and the like) and tissues correlates with and is indicative of lipid trafficking defects in neurons, and in particular, indicative of NPC disease.

B. Screening and Diagnosing Subjects Using Oxysterol Biomarkers.

In some embodiments of the present disclosure, a method for identifying a subject having, or at risk for, developing NPC disease is provided. The method may comprise quantifying or determining the concentration of one or more oxysterols in a biological sample obtained from the subject. The concentration of the one or more oxysterols in the tested biological sample collected from the subject can be compared with a reference value. Detection and quantification of elevated concentration(s) of one or more oxysterol(s) in the biological sample as compared to a reference value (which may be a predetermined value) can presumptively identify the subject as having, or at risk for developing, NPC disease.

In some embodiments, the present disclosure provides a method for identifying a subject having, or at risk of developing, NPC disease by an increased concentration of one or more oxysterols in a biological sample collected from the subject. According to some of these embodiments, steps for identifying a subject having NPC disease comprise: (a) obtaining a biological sample from the subject; (b) quantifying the concentration of oxysterols comprising 24-hydroxycholesterol, 7-ketocholesterol, cholestane-3β,5α,6β-triol or combinations thereof in the biological sample; and (c) comparing the concentration of the oxysterol present in the biological sample to a reference value of the oxysterol obtained from a control population, wherein if the concentration of the oxysterol from the subject is higher than the reference value, the subject can be identified as having, or at risk for developing, NPC disease. Diagnosis of NPC disease may also be determining using the methods of these embodiments.

In some embodiments, a biomarker can be any oxysterol that is elevated in NPC subjects and that can be reproducibly identified as elevated to a statistically significant degree when compared to a non-affected control population. Alternatively or additionally, a non-afflicted control population can also include one or more subject groups with wild-type, NPC1$^{-/+}$, NPC1$^{+/+}$, NPC2$^{-/+}$, and NPC2$^{+/+}$ genotypes not having any symptoms or effects of NPC disease. The superscript "minus sign" can denote and mutation within the NPC1 or NPC2 genomic regions.

Illustrative examples of oxysterols useful as biomarkers for NPC disease include 24-HC, 7-keto and triol oxysterol, the chemical structures of which are shown in FIGS. 1A-1C. In some embodiments of the present disclosure, 24-HC, 7-keto and triol oxysterol concentrations from biological samples may be used to identify, screen, diagnose, and/or monitor NPC disease in subjects, including subjects suspected of having the disease and/or subjects diagnosed with the disease.

In some embodiments, elevated 7-keto or triol levels, or combinations thereof, can differentiate NPC subjects from subjects with other lysosomal storage diseases, including lysosomal storage diseases with CNS involvement. For example, as shown in FIG. 8A, levels of 7-keto are statistically greater in samples from NPC subjects than in samples at least from subjects afflicted with infantile neuronal ceroid lipofuscinosis (INCL), GM 1 gangliosidosis (GM-1), GM-2 gangliosidosis (GM-2) (Tay-Sachs Disease), and hepatosplenomegaly (HSM). FIG. 8B shows that FIG. 8A, levels of triol are statistically greater in samples from NPC subjects than in samples at least from subjects afflicted with infantile neuronal ceroid lipofuscinosis (INCL), GM-1 gangliosidosis (GM-1), GM-2 gangliosidosis (GM-2) (Tay-Sachs Disease), Gaucher's disease (GD), and hepatosplenomegaly (HSM). The present disclosure provides methods that can distinguish subjects with NPC disease from subjects with other lysosomal storage diseases based on levels of 7-keto and triol. For example, the combination of elevated 7-keto and triol levels can differentiate NPC subjects from subjects with other lysosomal storage diseases to a statistically significant degree.

1. Reference Values.

A reference value represents a threshold value of oxysterol concentration to which a subject's measured oxysterol levels may be compared. The reference level can be selected based on the intended purpose of the test or assay being performed on the subject. For example, a reference level may be determined for purposes of identifying subjects affected by NPC while the same or different reference level may be used for monitoring the progression or severity of disease in a subject, or for screening a particular population of subjects for the disease, for example, neonatal subjects.

The selection of an appropriate reference level for a given test or assay is within the level of skill in the art. The choice of the reference value is not absolute. For example, a relatively low value may advantageously be used to reduce the incidence of false negatives, but may also increase the likelihood of false positives. Accordingly, as for other screening techniques, the reference value may be based on a number of factors, including but not limited to cost, the benefit of early diagnosis and treatment, the invasiveness of follow-up diagnostic methods for individuals that have false positive results, the intended purpose of the test or assay, the limits of accurate detection of oxysterol levels in the particular sample type, the prevalence and average or mean oxysterol levels of the relevant population, the desired level of statistical significance of the results, the level of quantification desired in terms of disease risk, presence, progression, or severity, and other factors that are routinely considered in designing screening assays.

In some embodiments, the reference or control level for each oxysterol can be based on known concentrations of each oxysterol in healthy and affected populations. The reference or control levels may be set as appropriate for the subject being screened. For example, oxysterol levels in a sample from a neonatal subject can be compared with oxysterol levels in a healthy and/or affected neonatal population. In other embodiments, the oxysterol levels identified in a subject can be compared with a matched unselected population. In some embodiments, the subject can be compared with a matched population of unaffected (i.e., healthy) subjects and/or a matched population of affected subjects. In some embodiments, the control population can be a matched control population wherein the control population is matched to the subject by gender and/or age.

As a non-limiting example of the selection of a reference value, subjects that have one or more of the oxysterol biomarkers selected from 24-HC, 7-keto and triol having values above about the 70th percentile, 75th percentile, 80th percentile, 90th percentile, 95th percentile, 96th percentile, 97th percentile, 98th percentile, 99th percentile, or higher, as compared with an appropriate control population may be presumptively identified as affected with NPC disease.

Alternatively or additionally, subjects having more than about 2, 3, 4, 5, 8, 10 or 20 fold higher oxysterol biomarker concentration than the average (alternatively, mean or median) value for an appropriate unaffected population as measured under similar or identical conditions may be presumptively identified as affected with NPC disease. In some cases, the diagnosis or identification of NPC corresponds to an oxysterol concentration that is above the reference value, even if the identified concentration of oxysterol in the biological sample of the NPC identified subject is not at least 2 fold higher than the reference value.

An appropriate reference value may be determined in a variety of ways and at a variety of times. In some embodiments, the reference value can be a predetermined value, based for example, on prior tests and assays on healthy or affected subjects ranging from six individuals to greater than a thousand. In other embodiments, the reference value can be determined during the course of the assay. For example, samples from known unaffected and/or affected subjects may be run concurrently with the test samples and a reference value determined therefrom. In some embodiments, test samples from a mixed population can be analyzed, and the reference value can be determined based on the distribution of the results using statistical methods known in the art.

2. Subjects.

In general, the methods for identifying, screening or monitoring the progression and/or treatment efficacy disclosed herein have experimental, veterinary and medical applications. Accordingly, subjects may be humans, primates, simians, canines, felines, equines, bovines, ovines, caprines, porcines, lagomorphs, rodents, avians, and the like. Subjects according to the present disclosure can be human neonatal (i.e., from the time of birth to about one week post-natal), infant, juvenile, adolescent or adult subjects. In some embodiments, neonatal subjects can be screened for the presence or risk of NPC disease. As used herein, "neonatal" subjects can include premature infants, as that term is used in the art.

The subjects may be part of a general population, e.g., for a broad-based screening assay. Alternatively, the subject may be one that may have an enlarged liver or spleen, or is suspected of having a lysosomal cholesterol storage or trafficking disorder by one or more clinical symptoms. The subject may also be experimentally determined to be accumulating one or more oxysterols or present other clinical symptoms (e.g., elevated expression of one or more oxysterols in one of blood, plasma, serum, cerebrospinal fluid and cell membranes such as red blood cell membranes). In other embodiments, subjects have already been diagnosed as having NPC disease, for example, by detection of accumulation of one or more of 24-HC, 7-keto and triol, and the clinical condition of the patient and/or the efficacy of the treatment may be monitored.

3. Biological Samples.

As used herein, a "biological sample" can include any body fluid, tissue, or matter from the subject, for example and without limitation, whole blood, plasma, serum, red blood cells, cord blood, biopsy samples, cerebrospinal fluid, sputum, amniotic fluid, or other tissue, cell (including in vitro cultured cells), fluid, or other biological material in which oxysterol concentration or accumulation may be detected and quantified. The suitability of a particular body fluid, tissue, or matter for use in the methods described herein may be determined by testing a sample of the fluid, tissue, or matter obtained from a subject suspected of having, diagnosed with, or screened positively for a lysosomal cholesterol storage or trafficking disease (e.g., cholesterol storage diseases) including cytotoxic oxysterol accumulation (NPC).

Methods for extracting or obtaining a biological sample of each of the subjects described above are well known in the art of medical and veterinary science, for example, phlebotomy, heel stick of a neonatal subject or infant, or a tissue biopsy. The biological sample may be obtained by surgical methods or biopsy. The biological sample may be obtained by relatively noninvasive methods, which are less traumatic to the subject, and more suitable for a broad-based screening assay. In some embodiments, the biological sample can be a body fluid sample. Illustrative body fluid samples, include, but are not limited to, plasma, sera, blood (including cord blood, and maternal blood), sputum, amniotic fluid, cerebral spinal fluid, cellular membrane samples (for example red blood cell membranes), and the like.

Alternatively or additionally, the biological sample can be a cell, or tissue sample, including cultured cells (e.g., fibroblasts) or tissues, and conditioned medium or effusions collected from cells or tissues. Exemplary cells or tissues can include, hematopoietic cells (including red blood cells, leucocytes, lymphocytes and the like), neural cells (including neurons, microglial cells and astrocytes), muscle (including skeletal, smooth, cardiac and diaphragm), liver, kidney, lung, skin, foreskin, umbilical cells or tissue, and the like.

In some embodiments, the biological sample can be provided on a solid medium, e.g., a filter paper, swab, cotton, and the like. In some embodiments, the biological sample can be a dried blood or plasma sample from a neonatal subject, e.g., dried blood or plasma spots on neonatal screening cards (e.g., "Guthrie" cards).

4. Evaluation.

Subjects may be presumptively identified as having, or at risk for developing, NPC disease by methods described herein. In some embodiments, the concentration of one or more oxysterols in a biological sample obtained from a subject can be quantified or determined. The concentration of the one or more oxysterols in the tested biological sample collected from the subject can be compared with a reference value. Elevated concentration(s) of one or more oxysterol(s) in the biological sample as compared to a reference value (which may be a predetermined value) can presumptively identify the subject as having, or at risk for developing, NPC disease.

In some embodiments, additional or alternative diagnostic testing can be carried out to confirm the diagnosis in these subjects. Typically, such alternative or additional methodologies (e.g., restriction fragment length polymorphism ("RFLP"), polymerase chain reaction ("PCR") and other genetic tests on tissue biopsies) are more costly, time-consuming, and invasive than the screening methods disclosed herein. For example, subjects having one or more oxysterol levels above a reference value may be presumptively identified as affected with NPC disease, and selected for additional diagnostic testing to confirm this diagnosis, determine the severity of the disease, assess whether the subject may be affected with another neurodegenerative disorder or lysosomal cholesterol storage disorder, or may be a healthy subject giving a false positive result in the screening assay.

Other tests for confirming the identification of a subject as having NPC disease using the methods of the present disclosure can include one of three commonly used tests. First, a skin biopsy can be obtained from the presumptively identified NPC disease afflicted subject. The skin fibroblasts are cultured and then stained with filipin to detect lysosomal accumulation of unesterified cholesterol. This assay may be qualitative but not quantitative. Second, an assay which determines the rate of cholesterol esterification can be measured in the cultures skin fibroblasts. Low rates of esterification, as compared to reference cell lines, are indicative of NPC disease. Third, the gold standard is sequence analysis of the NPC1 and NPC2 genes. This method detects >95% of clinically suspected NPC cases. Because the entire genomic region is not sequenced, a small percentage of NPC cases with novel intronic mutations or regulatory mutations within non-coding regions may escape detection.

Methods discussed below regarding monitoring course, severity, or clinical status, determining the efficacy of treatment, and neonatal screening may also be useful for screening and diagnosing subjects using oxysterol biomarkers.

C. Monitoring Course, Severity, or Clinical Status Using Oxysterol Biomarkers.

The present disclosure provides methods for monitoring the clinical course of a subject that has already been positively diagnosed and/or is being simultaneously diagnosed as affected with a disorder involving the accumulation of an oxysterol, (for example at least one of 24-HC, 7-keto and triol), as this term is described above. The present disclosure provides that elevated oxysterol concentrations in biological samples (in particular, plasma, blood and sera) from affected subjects correlate with the clinical state of the affected subject.

Methods of the present disclosure can be used for monitoring the progression and/or stabilizing of NPC disease. In some embodiments, the increase in one or more oxysterols such as 7-keto and triol described herein correlates with NPC disease severity. Additionally or alternatively, the progression and/or remission of NPC disease can be measured by monitoring the concentration of one or more oxysterols, for example, 24-HC, 7-keto, and/or triol. Oxysterol concentrations may be elevated prior to the worsening of the disease in the affected subject, and thus may be used as an early indicator of stabilization.

In some embodiments, the level of 24-HC can be used to monitor the progression of NPC disease. The progress of NPC disease has been found to be inversely correlated with the concentrations of 24-HC after an initial elevation of 24-HC concentration above a 24-HC reference value obtained from a non-NPC afflicted control population. As an example, the clinical status of a subject and/or the severity of the NPC disease can be monitored in a subject or patient by measuring the increase in one or more oxysterol species and the decrease of the oxysterol 24-HC.

Reference values, subjects, biological samples, and evaluation discussed above for screening and diagnosis of NPC disease are also applicable to the embodiments relating to monitoring course, severity, or clinical status. Methods discussed herein regarding screening and diagnosis, determining the efficacy of treatment, neonatal screening, and differentiating NPC from other lysosomal storage diseases may also be useful for monitoring course, severity, or clinical status using oxysterol biomarkers.

D. Determining the Efficacy of Treatment Using Oxysterol Biomarkers.

The clinical condition of the subject may be monitored to determine the efficacy of a treatment regime, e.g., enzyme replacement therapy, gene therapy, pharmaceutical intervention (for example treatments with one or more of: statins or other cholesterol synthesis inhibitors, cycloheximide, liver X receptor (LXR) agonists, orphan nuclear receptor PXR ligands, neurosteroids, N-butyldeoxynojirimycin (NB-DNJ) (miglusta), curcumin, chemical chaperones, antibiotics, salsalate, salicylic acid, RXR ligands, sphingolipid synthesis inhibitors (myriocin), KCl, EGTA, calcium channel inhibitors, nifedipine, verapamil, antioxidants (e.g., N-acetyl cysteine), vitamin E, vitamin C, aurinticarboxylic acid, flavonoids, cyclodextrins, estrogens, propyl gallate, glutathione, caspase inhibitors, MAP kinase inhibitors, peroxisome proliferator-activated receptor (PPARs) ligands, 15d-PGJ2, WY 14643, indomethacin, glucocorticoids, dexamethasone, hydrocortisone, PI-3 kinase inhibitors, NMDA open channel blockers) and/or dietary therapy. For example, if the level of one or more oxysterol biomarkers suggests that the current therapeutic regime may not be effective, or not efficacious, it may be determined to initiate an altered course of treatment. Alternatively or additionally, the condition of the subject may be monitored to determine whether to commence or re-initiate treatment of the subject.

The present disclosure provides methods for evaluating the efficacy of treatment by monitoring the concentration of one or more oxysterols, for example, 24-HC, 7-keto and triol during the course of treatment. In some embodiments, treatment efficacy can be generally correlated with a decrease in the concentration of 7-keto and/or triol oxysterol species. Specific method steps can include (a) obtaining a biological sample from a subject at a time ($T_0$) prior to or while being treated; (b) obtaining a biological sample from the subject at a time ($T_1$) subsequent to time ($T_0$); (b) quantifying the concentration of an oxysterol comprising 24-hydroxycholesterol, 7-ketocholesterol, cholestane-3β,5α,6β-triol or combinations thereof in the biological samples obtained at ($T_0$) and ($T_1$); and (c) comparing the concentration of the oxysterol present in the biological samples obtained at $T_0$ and $T_1$; wherein if the concentration of the oxysterol 7-ketocholesterol or cholestane-3β,5α,6β-triol in the biological sample obtained at time ($T_1$) is greater than the oxysterol concentration of 7-ketocholesterol or cholestane-3β,5α,6β-triol in the biological sample obtained at time ($T_0$) or if the concentration of the oxysterol 24-hydroxycholesterol in the biological sample obtained at time ($T_1$) is less than the oxysterol concentration of 24-hydroxycholesterol in the biological sample obtained at time ($T_0$), then the treatment can be said to be not efficacious.

A decrease in the oxysterol concentration, for example 7-keto and/or triol, obtained from a subject or patient diagnosed with NPC disease as compared to an earlier measured 7-keto and/or triol oxysterol concentration indicates that the treatment is effective. Treatment efficacy can also be determined by measuring the concentration of 24-HC during the treatment period. In the initial stages of NPC disease there can be an increase of 24-HC over healthy controls, as the disease progresses and/or increases in severity, the concentration of 24-HC in the subject or patient decreases. In a subject or patient diagnosed NPC, if the treatment provides an increase or stabilization of 24-HC levels in an NPC patient during the course of treatment over an earlier measured concentration of 24-HC, the treatment can be said to be effective.

In some embodiments, the present disclosure provides a method to determine the efficacy of treatment for Niemann-Pick C disease in a subject. The method includes: (a) obtaining a biological sample from a subject at a time ($T_0$) concurrent with or prior to the commencement of treatment; (b) obtaining a biological sample from the subject at a time ($T_1$) subsequent to the commencement of treatment; (c) quantifying the concentration of an oxysterol comprising 24-hydroxycholesterol, 7-ketocholesterol, cholestane-3β,5α,6β-triol or combinations thereof in the biological samples obtained at ($T_0$) and ($T_1$); and (d) comparing the concentration of the oxysterol present in the biological samples obtained at $T_0$ and $T_1$. If the concentration of the oxysterol 7-ketocholesterol or cholestane-3β,5α,6β-triol in the biological sample obtained at time ($T_1$) is greater than the oxysterol concentration of 7-ketocholesterol or cholestane-3β,5α,6β-triol in the biological sample obtained at time ($T_0$) or if the concentration of the oxysterol 24-hydroxycholesterol in the biological sample obtained at time ($T_1$) is less than the oxysterol concentration of 24-hydroxycholesterol in the biological sample obtained at time ($T_0$), then the treatment is not efficacious.

The time lapsing between ($T_0$) and ($T_1$) can be determined by those of ordinary skill in the art, in particular, the subject's medical professional. While not wishing to be bound by theory, it is believed that altered expression of oxysterol biomarkers 24-HC, 7-keto and triol can be detected and measured as soon as 1 week. Therefore, the method for determining the efficacy of a treatment for Niemann-Pick C disease in a subject can include taking a biological sample at time 0 ($T_0$) before, or-concurrently with the commencement of treatment for NPC disease. Then the efficacy of the treatment can be determined by quantifying the concentration of one or more oxysterols using the methods described herein at a time ($T_1$) which may be at least 1 week, or at least 2 weeks, or at least 3 weeks, or at least 4 weeks, or at least 8 weeks or at least 3 months, or at least 6 months after the commencement of treatment.

Reference values, subjects, biological samples, and evaluation discussed above for screening and diagnosis of NPC disease are also applicable to the embodiments relating to determining the efficacy of treatment. Methods discussed herein regarding screening and diagnosis, monitoring course, severity, or clinical status, neonatal screening, and differentiating NPC from other lysosomal storage diseases may also be useful for screening and diagnosing subjects using oxysterol biomarkers.

E. Neonatal Screening Using Oxysterol Biomarkers.

Methods disclosed herein may be advantageously employed as part of a neonatal screening program to identify affected neonatal subjects, for example, in the neonatal intensive care unit so as to permit early medical intervention. Many neonatal screening programs rely on a unique method of specimen collection, in which blood from a heel prick is absorbed onto a neonatal screening card (e.g., a cotton-fiber filter paper). Several neonatal diseases are screened in these subjects during their first weeks of life, including phenylalanine hydroxylase deficiency, which causes phenylketonuria ("PKU"), and branched-chain ketoacid dehydrogenase deficiency, which causes maple syrup urine disease ("MSUD"). Such screening programs are effective and cause no or little discomfort to these delicate patients.

Methods of the present disclosure can be used to identify neonatal subjects that have elevated levels of an oxysterol biomarker above a reference value—e.g., a value of 24-HC and/or 7-keto and/or triol concentration above a reference value of each of the oxysterol concentrations from non-NPC afflicted controls, indicative of a metabolic defect in NPC disease.

The neonatal screening methods disclosed herein, including high throughput screening assays may further advantageously be performed concurrently or in parallel (i.e., from the same sample but not necessarily in the same assay) with other neonatal screening assays, for example, on neonatal blood samples or dried blood spots on neonatal screening cards. In some embodiments, a neonatal screening program can be based on quantifying or measuring oxysterols from other biological samples, as described above. For example, 24-HC, 7-keto and triol can be measured in blood (e.g., cord blood), plasma, serum, or in the membrane of the neonatal blood cells, for example red blood cells. In some embodiments, one blood draw from a neonatal subject can provide sufficient biological sample to validate the quantity of one or more oxysterols present in different biological samples, for example, plasma and red blood cells using the same or different testing methods.

Accordingly, in some embodiments of the present disclosure, a method for screening a neonatal subject for as disorder involving accumulation of one or more oxysterols comprising the step of quantifying or determining the concentration of oxysterol in a biological sample taken from the neonatal subject, wherein the detection of the oxysterol in the biological sample a concentration that is greater than a reference value of the same oxysterol identifies the neonatal subject as affected with the disorder.

In some embodiments, a method of screening a neonatal subject for NPC disease comprises the step of quantifying or determining the concentration of oxysterol in a blood sample taken from the neonatal subject, wherein the detection of the oxysterol in the biological sample at a concentration that is greater than a reference value identities the neonatal subject as affected with NPC disease.

The methods can include the steps: (a) obtaining a biological sample from the neonatal subject; (b) quantifying the concentration of an oxysterol comprising 24-hydroxycholesterol, 7-ketocholesterol, cholestane-3β,5α,6β-triol or combinations thereof in the biological sample; (c) providing a reference value of the oxysterol from a non-affected neonatal control population, wherein the reference value can be the concentration of the oxysterol obtained from the same type of biological sample as obtained from the subject; and (d) comparing the concentration of the oxysterol of the neonatal subject to the reference value, wherein if the concentration of the oxysterol from the neonatal subject is higher than the reference value, the neonatal subject can be identified as having, or at risk for developing, Niemann-Pick C disease.

In still further embodiments, methods as applied to diagnosing, monitoring of disease severity and determining the efficacy of treatment described above can also be applied to neonatal subjects.

In still further embodiments, described in more detail below, methods for quantifying an oxysterol concentration in a biological sample involving chemical derivitization of the oxysterol and tandem mass spectrometry are utilized as part of a neonatal screening program for NPC disease using oxysterols 24-HC, 7-keto and triol as biomarkers for the presence of the disease.

As described above, methods of neonatal screening may be at least partially automated. For example, once a sample is loaded onto an HPLC column or into a mass spectrometer, the data can be captured and analyzed using an automated system.

Reference values, subjects, biological samples, and evaluation discussed above for screening and diagnosis of NPC disease are also applicable to the embodiments relating to neonatal screening. Methods discussed herein regarding screening and diagnosis, monitoring course, severity, or clinical status, determining the efficacy of treatment, and differentiating NPC from other lysosomal storage diseases may also be useful for neonatal screening using oxysterol biomarkers.

F. Methods for Quantifying Oxysterol Concentration in Biological Samples

In some embodiments, the methods for quantifying oxysterol concentration on a biological sample can be simple, rapid, accurate, relatively non-invasive (e.g., non-surgical), sensitive, and preferably minimize interfering signals from molecules other than the oxysterols 24-HC, 7-keto and triol. The method for quantifying the concentration of the oxysterol can include: (a) adding a known amount of an oxysterol internal standard to a biological sample; (b) extracting the oxysterols from the biological sample; and (c) quantifying the extracted oxysterols using a chromatography procedure.

As used herein, a chromatography procedure or combination of chromatography procedures can be used to quantify the oxysterol concentration in the collected biological sample. Methods for isolating sterols, including cholesterol and oxidized cholesterol are known in the art. In some embodiments, the quantification step of the method of identifying a subject with NPC disease can include: determining the relative concentration of the oxysterol and internal standard in the biological sample by correlating the area under the curve obtained for the known amount of oxysterol internal standard with the area under the curve obtained for the one or more oxysterols. Such determination can be accomplished when the isolated and/or derivatized oxysterols are passed through a chromatography procedure operable to derive the relative abundance of each oxysterol being identified relative to the known amount of oxysterol internal standard. The relative quantities of each of the oxysterols and oxysterol internal standard separated and/or isolated during the chromatography procedure can be routinely determined using computers and other processing devices that can be integrated with the detection means used in the chromatography equipment, for example, infra red, visible light diffraction, UV detection, mass spectroscopy, mass ionization and other methods used to detect lipids, sterols and/or oxysterols passing through a chromatography column or component.

In some embodiments, the oxysterol quantification methodology may be compatible with existing screening assays and may be adaptable to automation and high throughput screening. Methods useful to determine the concentration of one or more oxysterols in a biological sample indicative of NPC and other lysosomal cholesterol storage and trafficking diseases (e.g., cholesterol storage diseases), may be carried out using any suitable methodology or combination of methodologies that detects the presence or absence of oxysterols, and preferably, methodologies which determine the concentration of the oxysterol. Illustrative methods include, but are not limited to, chromatographic methods (e.g., high performance liquid chromatography ("HPLC")), thin layer chromatography ("TLC"), liquid chromatography-mass spectrometry ("LC-MS"), gas chromatography-mass spectrometry ("GC-MS"), time-of-flight mass spectrometry ("TOF-MS"), tandem mass spectrometry ("TMS"), matrix assisted laser desorption ionization—mass spectrometry ("MALDI-MS"), electrospray ionization—tandem mass spectrometry ("ESI-TMS") and combinations of these mass spectrometry techniques with or without sterol derivatization. Schroepfer Jr., G. J, "Oxysterols: Modulators of Cholesterol Metabolism and Other Processes", (2000), Physiol. Rev. 80(1): 362-521, provides additional assays and methods which may be useful in oxysterol quantification and identification. In some embodiments, HPLC, GC/MS, TOF-MS, and ESI-TMS can be used to determine the concentration of oxysterols in a biological sample. Further examples of quantification of oxysterol concentration from in vivo biological samples are described herein in the Examples section.

Jiang, X., et al. "Characterization of oxysterols by electrospray ionization tandem mass spectrometry after one-step derivatization with dimethylglycine" Rapid Commun. Mass Spectrom., (2007); 21: 141-152, describes high throughput screening methods for the detection identification and quantification of oxysterols using ESI-TMS. Such high throughput screening methods are useful in some embodiments of the present disclosure.

In some embodiments, the present disclosure provides methods that can be completely manual, alternatively and preferably, they are partially or completely automated. Screening programs to determine the concentration of oxysterols in a large number of biological samples, for example, a neonatal screening regime will generally be at least partially automated to facilitate high throughput of samples. The data can be captured and analyzed using an automated system. Other illustrative examples of high throughput methods can include arrays or micro-arrays of spotted biological samples (e.g., blood, plasma, serum, red blood cells and the like) on substrates which can be analyzed simultaneously. Such arrays or micro arrays can contain greater than about 10, 50, 100, 200, 300, 500, 800, 1000, 2000, 5000 samples or more.

In biological samples in which the concentration of the oxysterol can be low relative to the limits of detection of the technique, a derivatization step may be used prior to the step of detecting (alternatively, quantifying) oxidized cholesterol in the biological sample. In some embodiments, the derivatization step can also be performed after the oxysterols have been isolated or concentrated to yield higher quantities of oxysterols for quantification. The derivatization of oxysterols in the biological sample facilitates proper identification using the chromatography and mass spectrometry methods such as HPLC, LC-MS, GC-MS, TOF-MS, and ESI-TMS and may also be used to separate the oxysterol analyte from contaminants or interfering substances. Jiang, et al. supra provides additional protocols for the derivatization of oxysterol species in mixtures using ESI-TMS which may be useful in the present disclosure.

Referring to FIG. 2, the table below each mass spectra illustrates the relative concentration of each oxysterol which can be determined by calculating the area under the curve of each tested oxysterol in control and NPC affected representative samples relative to known amounts of an oxysterol internal standard, for example, D5-27-hydroxycholesterol. Such calculations can be automated and processed by the chromatographic software used. Relative concentrations of oxysterols found in various biological samples such as plasma (FIGS. 3A & 3B) and cerebrospinal fluid (FIG. 4) from NPC subjects and healthy control subjects using the methods described herein, illustrate the selectivity and specificity of the oxysterols 24-HC, 7-keto and triol as exquisite biomarkers for NPC disease.

G. Methods for Quantifying an Oxysterol in a Biological Sample Using Tandem Mass Spectrometry (TMS)

In some embodiments, the present disclosure further provides a method for quantifying or determining the concentration of oxysterols in a biological sample by ESI-TMS. In some embodiments, the oxysterols present in the biological sample (blood, plasma, serum or cell membrane) will need to be extracted and isolated from other substances; including substances that may interfere with the detection and/or quantification of oxysterol biomarkers. Methods for extracting oxysterols from complex mixtures are well known in the art. Conventionally, extraction of lipids from complex biological samples commences with a two-phase extraction with chloroform and methanol. In some embodiments, the organic phase of the two-phase extraction containing the oxysterols may be further purified using chromatography steps such as HPLC or passage through aminopropyl and silica columns to isolate a neutral sterol fraction prior to derivatization.

Derivatization of the oxysterols in the sample may be performed by any method known in the art, including derivatization using N,N-dimethylglycine, Girard P reagent and Pyridine:Hexamethyldisilazane:Trimethylchlorosilane in ratios of 5:2:1. In some embodiments, oxysterols can be saponified under mild conditions to avoid artificial oxysterol generation and derivatized with bis-(trimethyl-silyl)-trifluoroacetamide (BSTFA) and pyridine into trimethylsilyl ethers.

In some embodiments, matrix assisted laser desorption ionization—time of flight mass spectrometry ("MALDI-TOF MS"), GC-MS, LC-MS or ESI-TMS can be used to carry out the inventive methods described herein. Jiang, et al. supra provides additional protocols for the preparation, derivatization and identification of oxysterol species in mixtures using ESI-TMS which may be useful in the present disclosure.

Any suitable MS methodology known in the art may be employed, including, but not limited to GC-MS, LC-MS, Liquid Chromatography/Atmospheric Pressure Chemical Ionization Mass Spectrometric ("LC/APCI-MS"), ESI-MS, MALDI-MS and MALDI-TOF MS. Electrospray ionization, ion traps and ion cyclotron resonance equipped mass spectrometers can also be employed.

Further disclosed herein is an example of an ESI-TMS protocol for screening for NPC disease using one or more oxysterols as biomarkers to identify a subject as haring NPC or to be used as a screening method, for example, a neonatal screening method before the onset of clinical symptoms.

For the selective detection of compounds of a similar structural type, either a precursor ion scan function to identify the molecular species that fragment to a common product ion, or a constant neutral loss scan function to identify ions that lose a common fragment, or a multiple reaction monitoring where selected precursor and product ions only are detected can be employed. Addition of appropriate oxysterol internal standards, such as stable analogs, to the biological matrix before work-up and analysis facilitates accurate quantification of the target oxysterols.

An oxysterol internal standard can generally be added to the sample prior to manipulations, so that the standard can be subjected to the same conditions as the analyte. Any suitable internal standard may be used. For example, oxidized cholesterol homologs in which one of the carbons, for example at position 27 as in $D_5$-27-hydroxycholesterol, is hydroxylated can be used. The internal standard can be added to the sample in a known quantity. The ratio of signals produced by 24-HC, 7-keto, triol and other oxysterols that are elevated in NPC subjects and the internal standard will allow the starting quantity of the oxysterol biomarkers in the sample to be determined by use of a calibration curve. The calibration curve can be a plot of the signal ratio (oxysterol biomarkers of NPC to internal standard) against different known concentrations of 24-HC, 7-keto, triol standards, using the same fixed quantity of internal standard. In some embodiments, peak identification can be confirmed by relative retention time and mass spectral comparison with one or more authenticated oxysterol standards, as well as with the HP MS Chemstation NBS Mass Spectral Data Library of compounds.

In some embodiments of the present disclosure, a method for quantifying or determining oxysterol biomarkers in a biological sample comprises: (1) collecting a biological sample; (2) adding a known quantity of a suitable oxysterol standard to the sample; (3) extracting the oxysterols from the sample using a two-phase extraction medium; (4) purifying the oxysterol in the sample by normal phase chromatography, followed by elution from the column with a suitable solvent; (5) derivatization of the oxysterol and (6) quantification of the oxysterol biomarker using MS. A $D_5$-27-hydroxycholosterol standard can be used as an internal standard for the MS analysis.

The foregoing methodology can be employed in inventive screening and testing methodologies described above. As further described above, the methods may be partially or completely automated.

TMS based methodologies are particularly suitable for, quantifying or determining oxysterols 24-HC, 7-keto and triol as biomarkers for NPC disease in dried blood spots from neonatal screening cards. According to this embodiment, the method above further comprises a step of extracting the lipid component from the dried blood spot using a suitable solvent (e.g., an organic solvent or aqueous/organic mixture).

Thus, in some embodiments, the present disclosure provides a method of screening a neonatal subject for NPC disease, comprising: (1) providing a blood sample, comprising a dried blood spot on a solid absorbent substrate (e.g., a filter paper); (2) adding a known quantity of a suitable oxysterol standard to the sample; (3) extracting the oxysterols from the sample using a two-phase extraction medium; (4) purifying the oxysterol in the sample by normal phase chromatography, followed by elution from the column with a suitable solvent; (5) derivatization of the oxysterol and (6) quantification of the oxysterol biomarker using MS. A $D_5$-27-hydroxycholesterol standard can be used as an internal standard for the MS analysis; and (7) presumptively identifying those subjects as affected with NPC disease based on oxysterol concentrations in the biological sample that are greater than a reference value (as described above).

EXAMPLES

Aspects of the present disclosure may be further understood in light of the following examples, which should not be construed as limiting the scope of the present disclosure or the claims in any way.

Example 1

Isolation of Oxysterols from NPC Patient Samples 200 pmol of d5-27-hydroxycholesterol (27-HC), 50 µg butylated hydroxytoluene (BHT) and a magnetic flea bar are added to a 10 mL centrifuge tube. The tube is placed under a gentle stream of argon. 250 µL of plasma from a subject and 2.5 mL 0.35 M KOH is added to the tube. The tube is sealed tightly with a Teflon-lined screw cap, vortexed, and allowed to incubate for 2 hr at room temperature while stirring. After incubation, the flea bar is removed and the tube is centrifuged at 3000 rpm for 5 min to pellet the protein. The liquid phase of plasma mixture is removed and added to a 10 mL centrifuge tube placed under argon stream. The tube is then sealed tightly. The pH of liquid phase is lowered to approximately 7.0-8.0 using a 1:10 dilution of 85% $H_3PO_4$. While vortexing the centrifuge tube, 200 μL of $H_3PO_4$ is added dropwise to the plasma mixture until desired pH is achieved. 1.54 mL of 150 mM NaCl and 4.5 mL $CHCl_3$ is added to the plasma mixture. The tube is sealed with a Teflon screw cap, vortexed, and centrifuged at 3400 rpm for 5 min. The lower organic phase is extracted, transferred to a new 10 mL centrifuge tube, and placed under argon stream. 2.0 mL of $CHCl_3$ is added to the remaining aqueous phase of the first extraction, vortexed, and then centrifuged. The organic phases are collected from the centrifuge tubes and transferred to clean tubes under argon. The extraction steps above are then repeated. The pooled organic phases are evaporated under argon in a clean tube and sealed tightly with a Teflon-lined cap. The samples are then ready for oxysterol purification.

Example 2

Oxysterol Purification Using Aminopropyl and Silica Columns

The extracted lipid samples are resuspended in 250-300 μL $CHCl_3$ and then vortexed. One or more aminopropyl columns (Sep-Pak Vac RC 500 mg $NH_2$ Cartridges, part no. WAT054515) are primed with 4 mL hexane and are loaded with the lipid sample in $CHCl_3$. The sample drips into the column using gravity. The neutral fraction is eluted with 4 mL $CHCl_3$/isopropyl (2:1 v/v) and then dried under argon. The neutral fraction is resuspended in 1 mL toluene and the fraction is added to a silica column (Isolute 100 mg SI 10 mL XL cartridges, part no. 460-0010-G) primed with 4 mL hexane. The neutral fraction volume is pulled through the silica column (without drying out) using vacuum. The column is washed with 8 mL of 0.5% isopropyl in hexane, followed by elution of the neutral fraction with 2 mL of 30% isopropyl in hexane. The eluted fraction is collected and dried under argon. After silica column purification, the sample is resuspended in 250 μL of acetonitrile and transferred to a low retention/silanized microcentrifuge tube. The tube containing the eluted fraction is again washed with 250 μL acetonitrile and the resuspension added to a second microfuge tube. The eluted fraction containing the oxysterol component is then dried and sealed under argon.

Example 3

Derivatization of Oxysterols from Plasma Samples

To derivatize the oxysterols, a solution of 5:2:1 (v:v:v) of Pyridine: Hexamethyldisilazane:Trimethylchlorosilane is mixed in a centrifuge tube, vortexed, and the solution is centrifuged at 3400 rpm for 2 min. 100 μL of the derivatization solution is added to each of the samples prepared above containing the oxysterol component in eppendorf tubes. The eppendorf tubes are then sealed tightly, vortexed, and the derivatization solution and samples are incubated at 60° C. for 30 min. The reaction product containing the derivatized oxysterols is then dried down under a stream of argon. The derivatized oxysterols are resuspended in 100 μL heptane and the resuspension is then vortexed, centrifuged and transferred to an autosampler vial.

Example 4

Analysis of Oxysterol Profile by Gas Chromatography-Mass Spectrometry

The samples containing the derivatized oxysterols are run on an Agilent Technologies 5975B inert XL MSD with an Agilent Technologies 6890N Network GC System equipped with an Agilent Technologies 7683 Autosampler and an Agilent Technologies 7683B injector. A J&W Scientific 25 m model DB-1 column with an internal diameter of 0.2 mm and film thickness of 0.33 μm is used to separate the oxysterol species. 2.0 μL of sample is injected into the inlet, which is kept at 250° C. with a pressure of 28.98 psi. A split ratio of 10:1 is used, with a split flow of 10.6 in mL/min and a total flow of 15 mL/min within the inlet. The oven starts at 180° C. prior to ramping up to 250° C. at a rate of 20° C./min followed by an additional ramp up to 300° C. at a rate of 5° C./min where it stays for 15 min, allowing for an overall run time of 28.5 min. Initial flow of gasses through the column is set at 1.0 mL/min allowing for a nominal initial pressure of 28.04 psi and average velocity of 42 cm/sec. The MSD transfer line is kept at 280° C. throughout the sample run. The MS quadrupole is set to 150° C. and the MS source is set to 230° C. The MSD is set to monitor for 461.4, 544.4, 472.4, 456.4, and 413.4 ions at dwell times of 61 ms. FIG. 2 shows a gas chromatogram/mass spectrum (GC/MS) of oxysterols in plasma samples obtained from confirmed NPC patients and control non-NPC afflicted subjects.

Example 5

Oxysterol Concentration in Control and NPC Confirmed Subjects from Plasma Samples Thirty-three plasma samples were obtained from subjects with NPC disease enrolled in the natural history study at the National Institutes of Health. The plasma samples were collected in "purple-top" tubes containing $K_3$-EDTA and BHT. The tubes were immediately centrifuged and the plasma was isolated, stored in 1 ml aliquots and frozen at −80° C. The plasma samples were thawed immediately prior to analysis and the samples were processed as described above. The NPC plasma samples were analyzed for levels of d5-27-HC (internal standard), 27-HC, 24-HC (24-hydroxycholesterol), 7-ketocholesterol (7-keto), cholestane-3β,5α,6β-triol (triol), and 7α,27-HC (see FIG. 2). The results are presented in Table 1 below:

TABLE 1

Oxysterol quantification in control and NPC confirmed subjects from plasma samples using GC-MS.

| Oxysterol | NPC (ng/mL) | Control (ng/mL) | p value |
| --- | --- | --- | --- |
| 7α,27 | 9.79 | 9.95 | 0.875 |
| 7-keto | 455.14 | 106.06 | 2.98E−12 |
| 27-HC | 93.20 | 117.41 | 0.132 |
| 24-HC | 69.49 | 33.08 | 2.63E−09 |
| triol | 174.41 | 8.88 | 5.46E−17 |

A two-sample t-test assuming equal variance was used to test for significance between NPC patients and normal controls for 24-HC, 7α,27-HC and 7-keto. A two-sample t-test assuming unequal variance was used for triol. Three of the oxysterols (24-HC, 7-keto and triol) were significantly elevated in NPC subjects, as compared to normal controls, and thus represent plasma biomarkers for diagnosis of NPC disease.

The relationship between the oxysterol biomarkers and disease severity in the NPC subjects was also examined. Among the selected oxysterols, the concentration of 24-HC revealed a statistically significant inverse correlation between plasma levels of 24-HC and clinical disease severity (see FIG. 5). The Pearson correlation coefficient obtained was 0.67, with an $R^2$ value of 0.45 and a p value=0.0022. The concentration of 24-HC in a biological sample may be a useful biomarker for following NPC subjects longitudinally, and may provide a quantitative biomarker to follow efficacy of therapeutics interventions in slowing the progression of neurodegeneration in NPC subjects.

The stability of the oxysterols triol and 7-keto prepared in accordance with the methods of the present disclosure are shown in FIGS. 7A and 7B. Patient's having confirmed NPC disease were used to obtain plasma biological samples. The plasma biological samples were processed as described in Examples 1-4 except that some of the samples were not treated with butylated hydroxytoluene (BHT, a known antioxidant that prevents further oxidation of cholesterol), and either treated at room temperature or at 4° C. with and without BHT. The results show that the methods of the present disclosure can be performed at 4° C. or at room temperature and with and without BHT without adversely affecting the ability to isolate and quantify the presence of the oxysterols triol and 7-keto in the methods steps outlined in Example 1-4.

In addition to testing the stability of the oxysterols when isolated and determined using the methods of the present disclosure, the time of biological sampling, was also measured to determine whether there is a difference in the in vivo production by the subject of the oxysterols being identified. As shown in FIGS. 7A and 7B, there is no statistically beneficial or detrimental time to take a biological sample from the subject to be identified or screened for NPC disease. The data appears to indicate that the production of oxysterols triol and 7-keto is fairly constant throughout a 24 hour day.

Example 5

Specificity of the Oxysterols 7-Keto and Triol to Identify NPC Disease from Other Lysosomal Storage and Trafficking Diseases Oxysterols 7-keto and triol from a variety of human subjects having a lysosomal storage or trafficking disease including those with known CNS involvement: infantile neuronal ceroid lipofuscinosis (INCL), GM1 gangliosidosis (GM-1), GM-2 gangliosidosis (GM-2) (Tay-Sachs Disease), Gaucher's disease (GD) and hepatosplenomegaly (HSM). As shown in FIGS. 6A and 6B, the combination of elevated 7-keto and triol levels was able to differentiate NPC subjects from subjects with other LSDs. The concentration of the oxysterol 7-keto and triol are expressed as nanograms per milliliter (ng/mL) of plasma. The results depicted in FIGS. 8A and 8B for the oxysterols 7-keto and triol respectively, demonstrate that for identifying and screening purposes, (e.g., in human subjects), the oxysterols 7-keto and triol can be used as selective biomarkers to identify and screen NPC subjects from other subjects having a lysosomal storage or trafficking disease.

Example 6

Determination of Oxysterols in NPC and Wild-Type Mice

The present methods for quantifying the presence of oxysterols from NPC afflicted subjects, including NPC1−/− mice and wild-type non-afflicted NPC mice were performed to determine the expression of various oxysterols in these population. Measurements of various plasma oxysterols in the NPC1-deficient and wild type mice from ages 4-10 weeks were performed. Note that for these oxysterols, the divergence is generally greatest after 7 weeks when the mice are most symptomatic. Methods for isolating and quantifying the levels of oxysterols in the wild-type and NPC1 null mice are described herein.

As shown in FIG. 9, significant elevations in plasma 25-hydroxycholesterol (25-HC) and cholestane-3β,5α,6β-triol (triol) in NPC1 mice as compared to wild-type mice were observed at all time points. Even more striking was the separation in the plasma oxysterol levels (4β-hydroxycholesterol (4β-HC), 7α-hydroxycholesterol (7α-HC), 7β-hydroxycholesterol (7β-HC), and 7-keto), between wild-type and NPC1 mice beginning at 7-8 weeks of age, when the NPC1 mice begin losing weight and are overtly symptomatic. The elevated plasma oxysterols in the NPC1 null mice were corroborated by increased oxysterol levels in cerebellar and liver tissues. Remarkably, elevated triol levels in cerebellar tissue were detected as early as postnatal day 8 in the NPC1 mice, when the mice are asymptomatic yet display neuronal cholesterol storage. Taken together, these findings indicate that plasma levels of non-enzymatically generated oxysterols, including 25-HC, triol, 4β-HC, 7α-HC, 7β-HC, and 7-keto can be used to distinguish between wild-type and NPC1 disease, and may vary with disease progression. These oxysterols can be used as biomarkers for the identification and monitoring of NPC disease and its progression.

The foregoing description of the embodiments has been provided for purposes of illustration and description. It is not intended to be exhaustive or to limit the scope of the disclosure or claims. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the scope of the disclosure or claims, and all such modifications are intended to be included within the scope of the disclosure and claims.

What is claimed is:
1. A method for determining efficacy of a cyclodextrin therapy in a subject afflicted with a disorder involving the accumulation of one or more oxysterols, comprising:
 (a) obtaining at least one first body fluid sample from the subject prior to administering a cyclodextrin to the subject;
 (b) administering the cyclodextrin to the subject;
 (c) obtaining at least one second body fluid sample from the subject after the administering the cyclodextrin;
 (d) subjecting the at least one first body fluid sample to a first chromatography-mass spectroscopy analysis to determine concentration of 24-hydroxycholesterol;
 (e) subjecting the at least one second body fluid sample to a second chromatography-mass spectroscopy analysis to determine concentration of 24-hydroxycholesterol; and
 (f) determining magnitude of difference between the 24-hydroxycholesterol concentration of the at least one first body fluid sample and the at least one second body fluid sample, whereby an increase or stabilization of 24-hydroxycholesterol concentration in the second sample compared to the first sample indicates efficacy of the cyclodextrin therapy.

2. A method in accordance with claim 1, wherein each of the first chromatography-mass spectroscopy analysis and the second chromatography-mass spectroscopy analysis comprises:
 (a) adding to the body fluid sample a known amount of an internal standard comprising an oxysterol other than 24(S)-hydroxycholesterol;
 (b) isolating 24(S)-hydroxycholesterol from the biological sample; and
 (c) quantifying the isolated 24(S)-hydroxycholesterol.

3. A method in accordance with claim 2, wherein the quantifying 24(S)-hydroxycholesterol comprises determining the relative concentration of 24(S)-hydroxycholesterol and the known amount of internal standard in the body fluid sample by correlating the area under the curve obtained for the 24(S)-hydroxycholesterol with the area under the curve obtained for the internal standard.

4. A method in accordance with claim 1, wherein the first biological sample and the second biological are each selected from the group consisting of plasma, serum, blood, sputum and amniotic fluid.

5. A method in accordance with claim 1, wherein the body fluid sample is selected from the group consisting of plasma, serum and blood.

6. A method in accordance with claim 1, wherein each of the first chromatography-mass spectroscopy analysis and the second chromatography-mass spectroscopy analysis is a liquid chromatography-mass spectroscopy analysis.

7. A method in accordance with claim 1, wherein the disorder involving the accumulation of an oxysterol is selected from the group consisting of a lysosomal storage disease, a cholesterol trafficking disease, a neurodegenerative disease and a combination thereof.

8. A method in accordance with claim 1, wherein the disorder involving the accumulation of an oxysterol is selected from the group consisting of Niemann-Pick C (NPC) disease, infantile neuronal ceroid lipofuscinosis, GM1 gangliosidosis ("GM-1"), GM-2 gangliosidosis ("GM-2"), Gaucher's disease and hepatosplenomegaly.

9. A method in accordance with claim 8, wherein the GM-2 gangliosidosis ("GM-2") is Tay-Sachs disease.

10. A method in accordance with claim 1, wherein the disorder involving the accumulation of an oxysterol is Niemann-Pick C (NPC) disease.

11. A method for determining efficacy of a cyclodextrin therapy in a subject afflicted with a disorder involving the accumulation of one or more oxysterols, comprising:
 (a) obtaining at least one first body fluid sample from the subject prior to administering a cyclodextrin to the subject;
 (b) administering the cyclodextrin to the subject;
 (c) obtaining at least one second body fluid sample from the subject after the administering the cyclodextrin;
 (d) subjecting the at least one first body fluid sample to a first chromatography-mass spectroscopy analysis to determine concentration of cholestane-3β,5α,6β-triol;
 (e) subjecting the at least one second body fluid sample to a second chromatography-mass spectroscopy analysis to determine concentration of cholestane-3β,5α,6β-triol; and
 (f) determining magnitude of difference between the cholestane-3β,5α,6β-triol concentration of the at least one first body fluid sample and the at least one second body fluid sample, whereby a reduction in cholestane-3β,5α,6β-triol concentration in the second sample compared to the first sample indicates efficacy of the cyclodextrin therapy.

12. A method in accordance with claim 11, wherein each of the first chromatography-mass spectroscopy analysis and the second chromatography-mass spectroscopy analysis comprises:
 (a) adding to the body fluid sample a known amount of an internal standard comprising an oxysterol other than cholestane-3β,5α,6β-triol;
 (b) isolating cholestane-3β,5α,6β-triol from the biological sample; and
 (c) quantifying the isolated cholestane-3β,5α,6β-triol.

13. A method in accordance with claim 12, wherein the quantifying cholestane-3β,5α,6β-triol comprises determining the relative concentration of cholestane-3β,5α,6β-triol and the known amount of internal standard in the body fluid sample by correlating the area under the curve obtained for the cholestane-3β,5α,6β-triol with the area under the curve obtained for the internal standard.

14. A method in accordance with claim 11, wherein the first biological sample and the second biological are each selected from the group consisting of plasma, serum, blood, sputum and amniotic fluid.

15. A method in accordance with claim 11, wherein the body fluid sample is selected from the group consisting of plasma, serum and blood.

16. A method in accordance with claim 11, wherein each of the first chromatography-mass spectroscopy analysis and the second chromatography-mass spectroscopy analysis is a liquid chromatography-mass spectroscopy analysis.

17. A method in accordance with claim 11, wherein the disorder involving the accumulation of an oxysterol is selected from the group consisting of a lysosomal storage disease, a cholesterol trafficking disease, a neurodegenerative disease and a combination thereof.

18. A method in accordance with claim 11, wherein the disorder involving the accumulation of an oxysterol is selected from the group consisting of Niemann-Pick C (NPC) disease, infantile neuronal ceroid lipofuscinosis, GM1 gangliosidosis ("GM-1"), GM-2 gangliosidosis ("GM-2"), Gaucher's disease and hepatosplenomegaly.

19. A method in accordance with claim 18, wherein the GM-2 gangliosidosis ("GM-2") is Tay-Sachs disease.

20. A method in accordance with claim 11, wherein the disorder involving the accumulation of an oxysterol is Niemann-Pick C (NPC) disease.

* * * * *